(12) United States Patent
    Wada

(10) Patent No.: US 10,729,505 B2
(45) Date of Patent: Aug. 4, 2020

(54) MEDICAL SYSTEM

(71) Applicant: OLYMPUS CORPORATION, Tokyo (JP)

(72) Inventor: Toru Wada, Saitama (JP)

(73) Assignee: OLYMPS CORPORATION, Tokyo (JP)

( * ) Notice: Subject to any disclaimer, the term of this patent is extended or adjusted under 35 U.S.C. 154(b) by 0 days.

(21) Appl. No.: 16/220,038

(22) Filed: Dec. 14, 2018

(65) Prior Publication Data

US 2019/0117326 A1    Apr. 25, 2019

Related U.S. Application Data

(63) Continuation of application No. PCT/JP2016/068639, filed on Jun. 23, 2016.

(51) Int. Cl.
    *A61B 34/00*    (2016.01)
    *A61B 34/30*    (2016.01)
    (Continued)

(52) U.S. Cl.
    CPC .............. *A61B 34/74* (2016.02); *A61B 1/313* (2013.01); *A61B 34/25* (2016.02); *A61B 34/30* (2016.02);
    (Continued)

(58) Field of Classification Search
    CPC ......... A61B 34/74; A61B 90/39; A61B 1/313; A61B 34/70; A61B 34/35; A61B 60/06;
    (Continued)

(56) References Cited

U.S. PATENT DOCUMENTS 5,876,325 A    3/1999 Mizuno et al.
9,101,397 B2 *    8/2015 Guthart .................. A61B 34/30
(Continued)

FOREIGN PATENT DOCUMENTS

EP    1980194 A1    10/2008
EP    3103411 A1    12/2016
(Continued)

OTHER PUBLICATIONS

International Search Report dated Sep. 20, 2016 issued in PCT/JP2016/068639.

*Primary Examiner* — Susan E. Hodges
(74) *Attorney, Agent, or Firm* — Scully, Scott, Murphy & Presser, P.C.

(57) ABSTRACT

A medical system including: a first manipulator inserted into a lumen of a patient, the first manipulator including a first end effector and a first camera configured to capture an image of the first end effector; a second manipulator inserted into an abdominal cavity of the patient, the second manipulator including a second camera; a first operating portion configured to operate both the first and second manipulators; a first selector configured to select one of the first and second manipulators as a first operating target; a controller configured to control the first and second manipulators; and a display configured to display to the operator, wherein the controller includes one or more processors, the one or more processors are configured to: acquire the selected first operating target, acquire a first image from the first or second camera, and transmit the acquired first image so as to be displayed on the display.

16 Claims, 26 Drawing Sheets

(51) Int. Cl.
  *A61B 90/00* (2016.01)
  *A61B 1/313* (2006.01)
  *A61B 34/35* (2016.01)
  *A61B 18/14* (2006.01)
  *A61B 1/00* (2006.01)

(52) U.S. Cl.
  CPC .............. *A61B 34/35* (2016.02); *A61B 34/70* (2016.02); *A61B 90/06* (2016.02); *A61B 90/361* (2016.02); *A61B 90/37* (2016.02); *A61B 90/39* (2016.02); *A61B 1/00149* (2013.01); *A61B 18/1445* (2013.01); *A61B 2018/1412* (2013.01); *A61B 2034/301* (2016.02); *A61B 2034/303* (2016.02); *A61B 2090/364* (2016.02)

(58) Field of Classification Search
  CPC ....... A61B 34/25; A61B 90/361; A61B 90/37; A61B 34/30; A61B 2090/364; A61B 2018/1412; A61B 18/1445; A61B 2034/301; A61B 2034/303; A61B 1/00149; A61B 2034/2048
  USPC .......................................................... 348/65
  See application file for complete search history.

(56) References Cited

U.S. PATENT DOCUMENTS

| | | |
|---|---|---|
| 2005/0215854 A1 | 9/2005 | Ozaki et al. |
| 2007/0161855 A1 | 7/2007 | Mikkaichi et al. |
| 2007/0167967 A1 | 7/2007 | Mikkaichi et al. |
| 2007/0255100 A1 | 11/2007 | Barlow et al. |
| 2008/0004603 A1 | 1/2008 | Larkin et al. |
| 2009/0036902 A1* | 2/2009 | DiMaio .................. A61B 34/10 606/130 |
| 2009/0192519 A1* | 7/2009 | Omori .................... A61B 34/30 606/130 |
| 2011/0202068 A1* | 8/2011 | Diolaiti ................... B25J 9/161 606/130 |
| 2014/0114481 A1 | 4/2014 | Ogawa et al. |
| 2014/0179997 A1 | 6/2014 | von Grunberg et al. |
| 2015/0119638 A1* | 4/2015 | Yu .......................... G16H 40/63 600/102 |
| 2016/0331473 A1 | 11/2016 | Yamamura |

FOREIGN PATENT DOCUMENTS

| | | |
|---|---|---|
| JP | H06-285042 A | 10/1994 |
| JP | H07-184909 A | 7/1995 |
| JP | H08-275958 A | 10/1996 |
| JP | 3384573 B2 | 3/2003 |
| JP | 2003-204967 A | 7/2003 |
| JP | 2003-204968 A | 7/2003 |
| JP | 2004-041580 A | 2/2004 |
| JP | 2007-296382 A | 11/2007 |
| JP | 2009-112644 A | 5/2009 |
| JP | 2009-523033 A | 6/2009 |
| JP | 2009-542362 A | 12/2009 |
| JP | 4698966 B2 | 6/2011 |
| JP | 4898709 B2 | 3/2012 |
| JP | 2013-017512 A | 1/2013 |
| JP | 2013-017513 A | 1/2013 |
| JP | 2015-146981 A | 8/2015 |
| JP | 2016-506261 A | 3/2016 |
| WO | WO 2007/081056 A | 7/2007 |
| WO | WO 2008/002830 A2 | 1/2008 |
| WO | WO 2013/005862 A1 | 1/2013 |

\* cited by examiner

MEDICAL SYSTEM

CROSS-REFERENCE TO RELATED APPLICATIONS

This is a continuation of International Application PCT/JP2016/068639, with an international filing date of Jun. 23, 2016, which is hereby incorporated by reference herein in its entirety.

TECHNICAL FIELD

The present invention relates to a medical system.

BACKGROUND ART

In the related art, there is a known surgical method in which treatment is performed by causing a treatment tool inserted into a lumen, such as the large intestine, and a treatment tool inserted into the abdominal cavity via a trocar to cooperate with each other (for example, see Patent Literature 1). In such a surgery, the treatment tool in the lumen and the treatment tool in the abdominal cavity are operated by separate operators.

CITATION LIST

Patent Literature

{PTL 1} Japanese Unexamined Patent Application, Publication No. 2015-146981

SUMMARY OF INVENTION

One aspect of the present invention is directed to a medical system including: a first manipulator inserted into a lumen of a patient, the first manipulator including a first end effector and a first camera configured to capture an image of the first end effector; a second manipulator inserted into an abdominal cavity of the patient, the second manipulator including a second camera; a first operating portion configured to operate both the first manipulator and the second manipulator; a first selector configured to select one of the first manipulator and the second manipulator as a first operating target of the first operating portion; a controller configured to control the first manipulator and the second manipulator; and a display configured to display to the operator, wherein the controller includes one or more processors, the one or more processors are configured to: acquire the first operating target selected by the first selector, acquire a first image from the first camera or the second camera provided in the acquired first operating target, and transmit the acquired first image so as to be displayed on the display.

Another aspect of the present invention is directed to a control method for a medical system including a first manipulator inserted into a lumen and a second manipulator inserted in an abdominal cavity, the control method including: acquiring one of the first manipulator and the second manipulator as a selected first operating target, acquiring a first image from a first camera of the first manipulator or a second camera of the second manipulator provided in the selected first operating target, and transmitting the first image so as to be displayed on a display.

DESCRIPTION OF EMBODIMENTS

First Embodiment

A medical system 100 according to a first embodiment of the present invention will be described below with reference to FIGS. 1 to 5.

Figure 1:
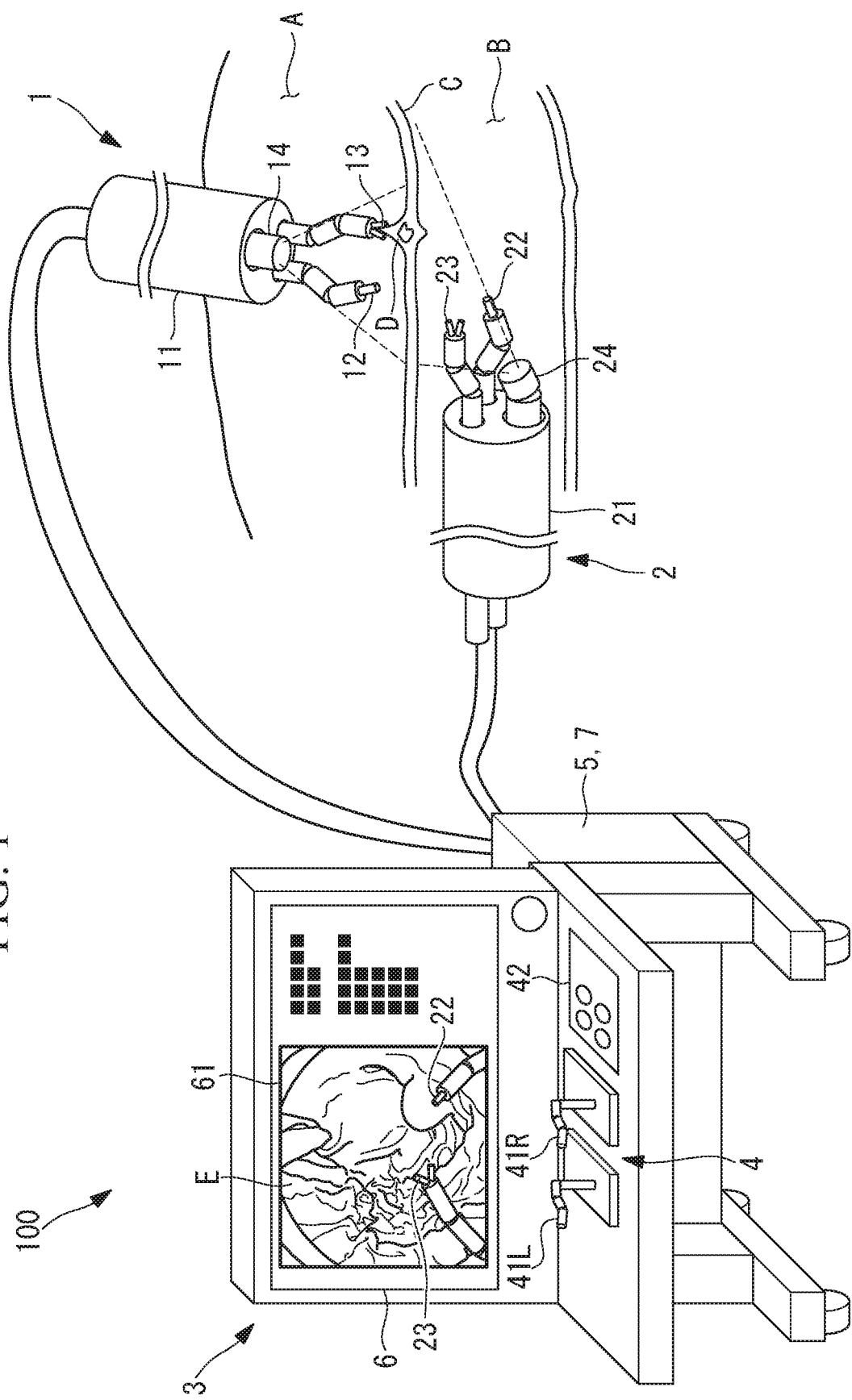
FIG. 1 is an external view showing the overall configuration of a medical system according to a first embodiment of the present invention.
Figure 2:
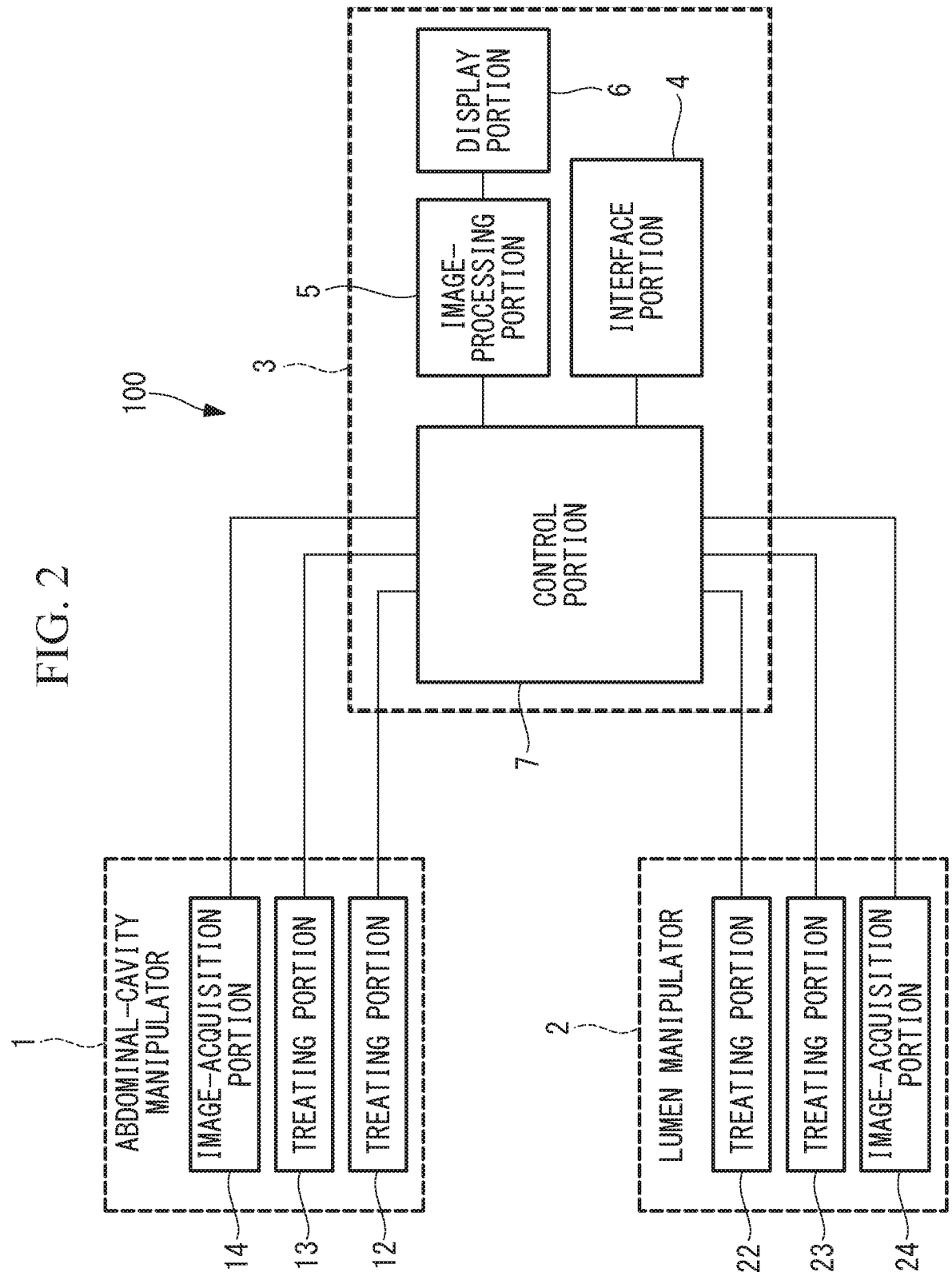
FIG. 2 is a block diagram showing the overall configuration of the medical system in FIG. 1.

As shown in FIGS. 1 and 2, the medical system 100 according to this embodiment is provided with two medical manipulators 1 and 2 that are inserted into a body and a console apparatus 3 that is disposed outside the body and with which an operator remotely operates the two manipulators 1 and 2.

One of the manipulators (first manipulator) is an abdominal-cavity manipulator 1 that is used in an abdominal cavity (first body cavity) A. The abdominal-cavity manipulator 1 is provided with: a long, thin arm 11 that is inserted into the abdominal cavity A; two electrically-powered treating portions (first treating portions) 12 and 13 that are provided at a distal end of the arm 11 and that are used to treat biological tissue; and an image-acquisition portion (first image-acquisition portion) 14 that is provided at the distal end of the arm 11 and that is used to observe the treating portions 12 and 13. An abdominal-cavity image (first image) L acquired by the image-acquisition portion 14 is transmitted to the console apparatus 3. The abdominal-cavity manipulator 1 is provided with driving portions (not shown) for electrically driving the treating portions 12 and 13, and the driving portions cause the treating portions 12 and 13 to perform motions in accordance with control signals from a control portion 7.

The other manipulator (second manipulator) is a lumen manipulator 2 that is used in a lumen (second body cavity) B, such as the digestive tract. The lumen manipulator 2 is provided with: a long, thin arm 21 that is inserted into the lumen B; two electrically-powered treating portions (second treating portions) 22 and 23 that are provided at a distal end of the arm 21 and that are used for treating biological tissue; and an image-acquisition portion (second image-acquisition portion) 24 that is provided at the distal end of the arm 21 and that is used to observe the treating portions 22 and 23. A lumen image (second image) E acquired by the image-acquisition portion 24 is transmitted to the console apparatus 3. The lumen manipulator 2 is provided with driving portions (not shown) for electrically driving the treating portions 22 and 23, and the driving portions cause the treating portions 22 and 23 to perform motions in accordance with control signals received from the control portion 7.

The console apparatus 3 is provided with: an interface portion 4 that is operated by the operator; an image-processing portion 5 that processes the abdominal-cavity image L and the lumen image E acquired by the image-acquisition portions 14 and 24; a display portion 6 that displays the images processed by the image-processing portion 5; and the control portion 7 that controls, in accordance with inputs to the interface portion 4, the motions of the treating portions 12, 13, 22, and 23 and the display on the display portion 6. The interface portion 4 and the display portion 6 are provided on a single work table, and are configured so that one operator operates the interface portion 4 while observing the abdominal-cavity image L and the lumen image E displayed on the display portion 6.

The interface portion 4 is provided with: two operating portions 41L and 41R for the operator to input operation instructions for the treating portions 12, 13, 22, and 23; and a single operating-target selecting portion 42 for selecting operating targets of the two operating portions 41L and 41R.

The two operating portions are constituted of the left operating portion 41L and the right operating portion 41R that correspond to the left hand and the right hand of the operator, respectively, and are disposed next to each other in the horizontal direction. The right operating portion 41R is associated with the treating portion 12 of the abdominal-cavity manipulator 1 and the treating portion 22 of the lumen manipulator 2. The left operating portion 41L is associated with the treating portion 13 of the abdominal-cavity manipulator 1 and the treating portion 23 of the lumen manipulator 2. The individual operating portions 41L and 41R are formed, for example, like arms and can be operated in multiple directions. As a result of the operator operating the operating portions 41L and 41R, operation signals indicating operation directions and operation amounts of the operating portions 41L and 41R are transmitted to the control portion 7 from the interface portion 4.

Figure 3:
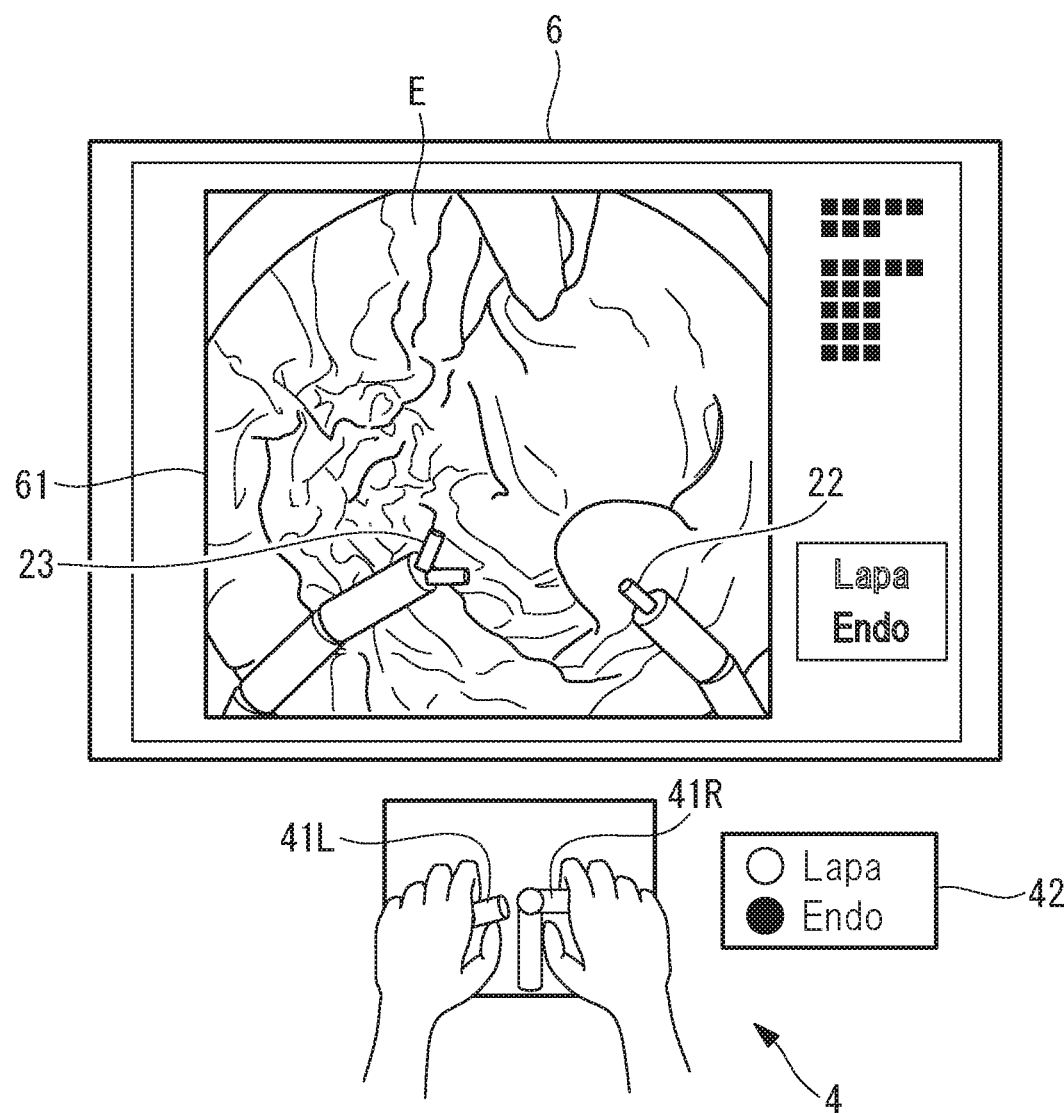
FIG. 3 is a diagram showing an interface portion and a display portion of the medical system in FIG. 1, and is a diagram for explaining a screen display in the case in which an operating target is a treating portion in a lumen.
Figure 4:
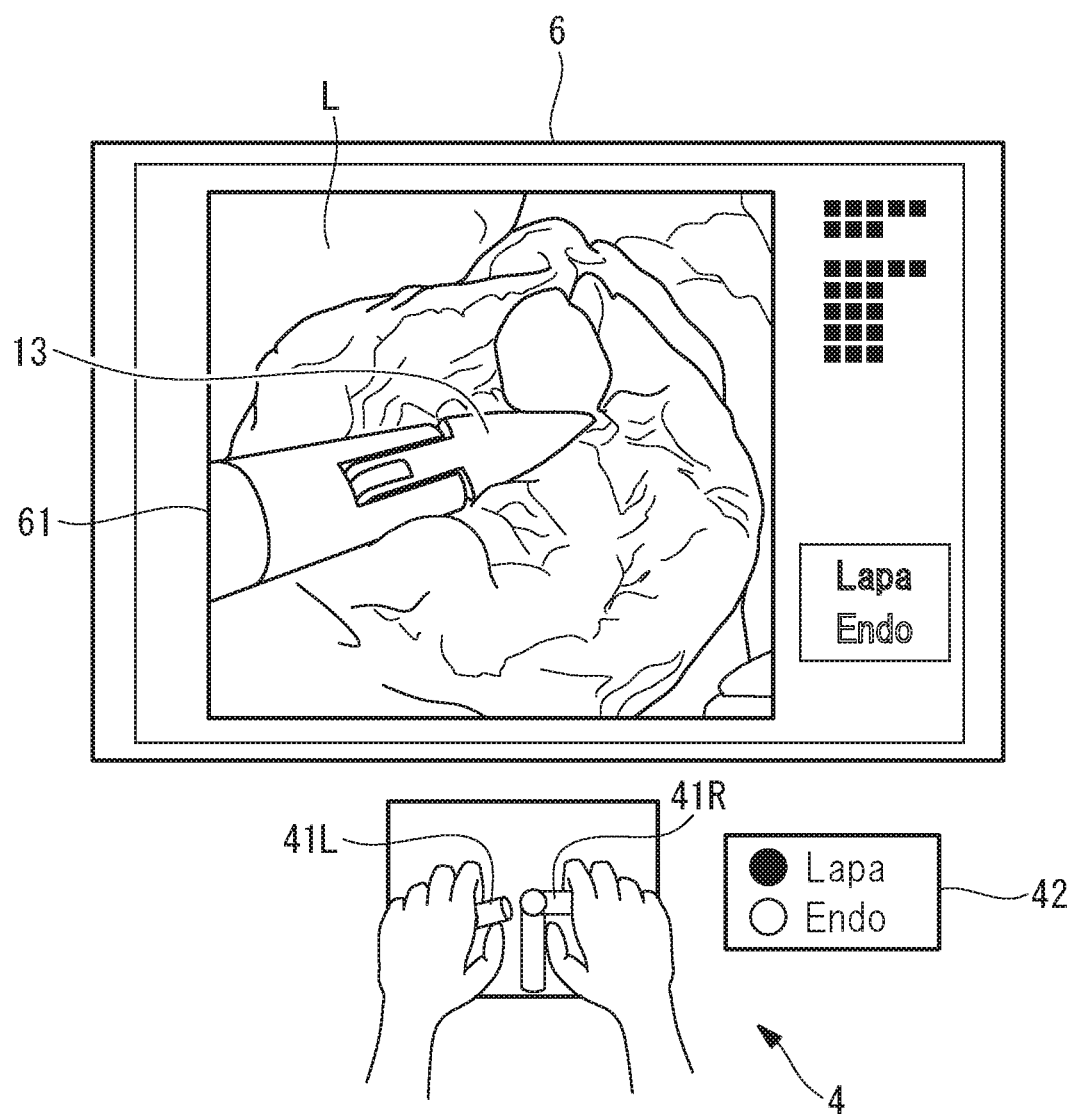
FIG. 4 is a diagram showing the interface portion and the display portion of the medical system in FIG. 1, and is a diagram for explaining the screen display in the case in which the operating target is a treating portion in an abdominal cavity.

As shown in FIGS. 3 and 4, the operating-target selecting portion 42 is configured so as to allow the operator to selectively select one of "Lapa" and "Endo" as the operating targets of the left operating portion 41L and the right operating portion 41R. "Lapa" indicates the treating portions 12 and 13 provided in the abdominal-cavity manipulator 1. "Endo" indicates the treating portions 22 and 23 provided in the lumen manipulator 2. FIG. 3 shows a state in which "Endo" is selected, and FIG. 4 shows a state in which "Lapa" is selected. Therefore, the operator can simultaneously operate the two treating portions 12 and 13 or 22 and 23 disposed in the same cavity A or B by using the left and right operating portions 41L and 41R. The operating-target selecting portion 42 transmits information about the operating targets selected by the operator (treating-portion selection information) to the control portion 7.

The display portion 6 has a single screen 61 that displays one of the abdominal-cavity image L and the lumen image E.

The control portion 7 identifies, on the basis of the treating-portion selection information received from the operating-target selecting portion 42, the two treating portions that are selected by the operator as the operating targets. Next, the control portion 7 generates control signals for driving the two identified treating portions 12 and 13 or 22 and 23 in accordance with the operation signals received from the interface portion 4, and transmits the control signals to the manipulator 1 or 2 having the operating targets.

Furthermore, of the abdominal-cavity image L and the lumen image E received from the manipulators 1 and 2, the control portion (display switching portion) 7 selects, as a display image, an image acquired by the image-acquisition portion 14 or 24 provided in the manipulator 1 or 2, which is the same manipulator as that which includes the operating targets on the basis of the treating-portion selection information. The control portion 7 transmits the display image to the display portion 6 via the image-processing portion 5, thus causing the image to be displayed on the screen 61. By doing so, of the abdominal-cavity image L and the lumen image E, the image in which the operating targets are captured is displayed on the screen 61.

The image-processing portion 5 applies, as appropriate, processing to the display image received from the control portion 7 and subsequently transmits the display image to the display portion 6.

Next, the operation of the thus-configured medical system 100 will be described in terms of an example case in which an affected portion D in a wall C of the lumen B is treated from an abdominal-cavity-A side and a lumen-B side.

In order to treat the affected portion D by using the medical system 100 according to this embodiment, the abdominal-cavity manipulator 1 inserted into the abdominal cavity A and the lumen manipulator 2 inserted into the lumen B are disposed at positions that substantially face each other with the wall C interposed therebetween. By doing so, the image-acquisition portion 14 acquires the abdominal-cavity image L in which the affected portion D is observed from the abdominal-cavity-A side, and the image-acquisition portion 24 acquires the lumen image E in which the affected portion D is observed from the lumen-B side. The abdominal-cavity image L and the lumen image E are individually transmitted to the control portion 7 in the console apparatus 3 from the manipulators 1 and 2. The control portion 7 is initially set so that a predetermined one of the abdominal-cavity image L and the lumen image E is selected as the display image and is displayed on the display portion 6.

When the operator desires to operate the treating portions 22 and 23 on the lumen-B side, he/she selects "Endo" by operating the operating-target selecting portion 42, as shown in FIG. 3. The treating-portion selection information indicating "Endo" is transmitted to the control portion 7 from the interface portion 4 (step SA1). The control portion 7 sets the operating targets to the treating portions 22 and 23 of the lumen manipulator 2 on the basis of the treating-portion selection information and controls the display on the screen 61 so that the lumen image E is displayed on the screen 61.

Figure 5:
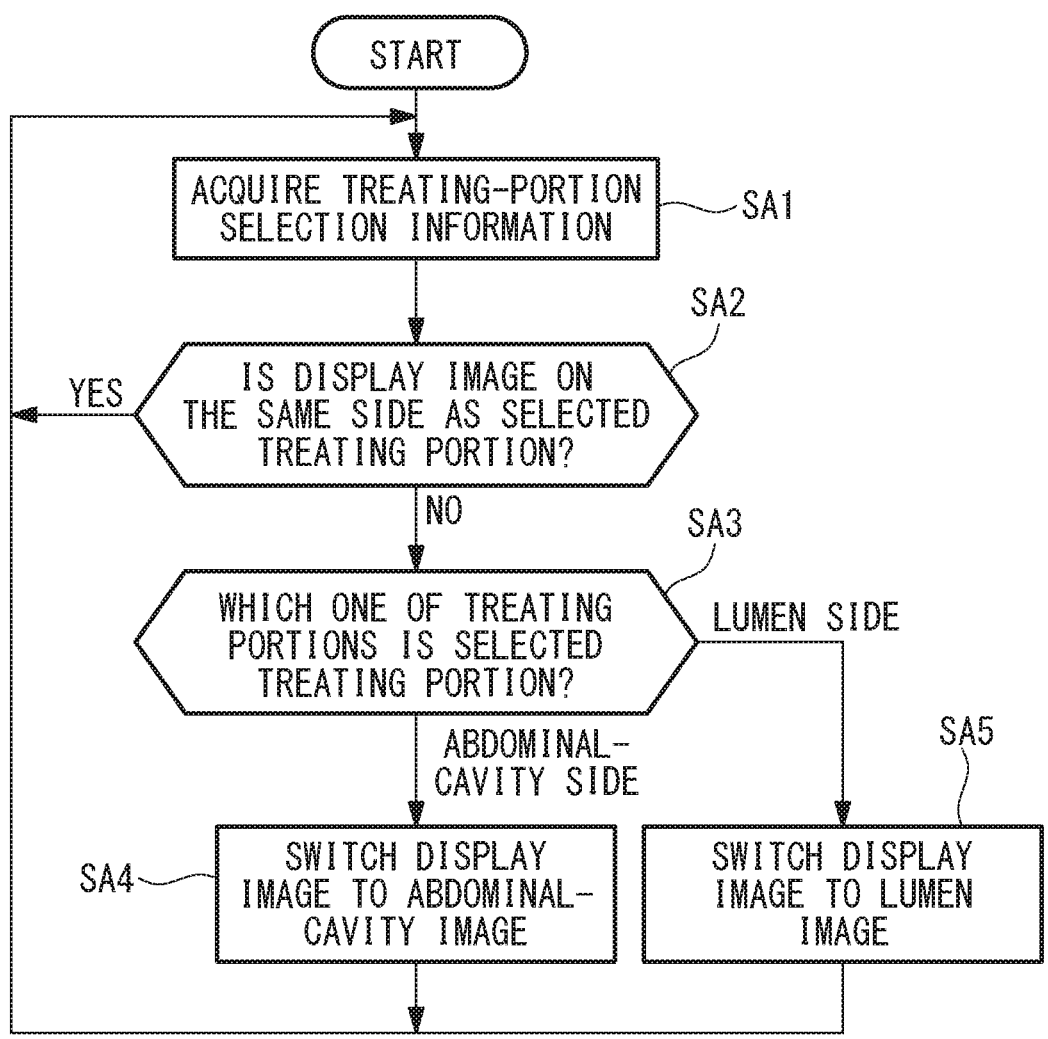
FIG. 5 is a flowchart showing a method for controlling the display in the medical system in FIG. 1.

Specifically, as shown in FIG. 5, the control portion 7 determines whether or not the current display image is the lumen image E (step SA2). In the case in which the current display image is the lumen image E and the lumen image E is displayed on the screen 61 ("YES" in step SA2), the state in which the lumen image E is selected is maintained. In the case in which the current display image is the abdominal-cavity image L, the control portion 7 switches the display image to the lumen image E from the abdominal-cavity image L ("LUMEN SIDE" in step SA3, and step SA5), thus causing the lumen image E to be displayed on the screen 61.

Doing so achieves a state in which it is possible for the operator to remotely operate the treating portions 22 and 23 by means of the operating portions 41L and 41R while observing the affected portion D and the treating portions 22 and 23 in the lumen image E on the screen 61.

On the other hand, when the operator desires to operate the treating portions 12 and 13 on the abdominal-cavity-A side, he/she selects "Lapa" by operating the operating-target selecting portion 42, as shown in FIG. 4. The treating-portion selection information indicating "Lapa" is transmitted to the control portion 7 from the interface portion 4. The control portion 7 sets the operating targets to the treating portions 12 and 13 of the abdominal-cavity manipulator 1 on the basis of the treating-portion selection information and controls the display on the screen 61 so that the abdominal-cavity image L is displayed on the screen 61.

Specifically, in the case in which the current display image is the lumen image E ("NO" in step SA2), the control portion 7 switches the display image to the abdominal-cavity image L from the lumen image E ("ABDOMINAL-CAVITY SIDE" in step SA3, and step SA4), thus causing the abdominal-cavity image L to be displayed on the screen 61.

Doing so achieves a state in which it is possible for the operator to remotely operate the treating portions 12 and 13 by means of the operating portions 41L and 41R while observing the affected portion D and the treating portions 12 and 13 in the abdominal-cavity image L on the screen 61.

As has been described above, with this embodiment, it is possible to switch the operating targets of the operating portions 41L and 41R between the treating portions 12 and 13 in the abdominal cavity A and the treating portions 22 and 23 in the lumen B. By doing so, there is an advantage in that it is possible for one operator to operate, via the single interface portion 4, the two sets of treating portions 12, 13, 22, and 23 that are disposed in the cavities A and B separated by the wall C.

Furthermore, of the abdominal-cavity image L and the lumen image E, the image in which the treating portions serving as the operating targets are captured is automatically displayed on the screen 61. Thus, when the operator switches the operating targets, the display on the screen 61 is also automatically switched to the image on the operating-target side. By doing so, there is an advantage in that the one operator can smoothly operate the two sets of treating portions 12, 13, 22, and 23 by causing said treating portions to cooperate with each other while ascertaining the states of both the treating portions 12 and 13 in the abdominal cavity A and the treating portions 22 and 23 in the lumen B.

In this embodiment, the two treating portions 12 and 13 or 22 and 23 are provided in each of the manipulators 1 and 2, and the two operating portions 41L and 41R are provided in the interface portion 4; however, the number of treating portions in each of the manipulators 1 and 2 and the number of operating portions may each be one or three or greater. In addition, the number of treating portions in the abdominal-cavity manipulator 1 and the number of treating portions in the lumen manipulator 2 may be different from each other.

Note that, although detailed descriptions are omitted, the treating portions that are not selected are held in the state that said treating portions were in immediately before being switched. The treating portions that are not selected may perform motions in accordance with motions set in advance.

Second Embodiment

Next, a medical system according to a second embodiment of the present invention will be described with reference to FIGS. 6 to 8.

In this embodiment, points that differ from the first embodiment will mainly be described, and the configurations that are the same as those of the first embodiment will be given the same reference signs, and the descriptions thereof will be omitted.

In the first embodiment, the operating targets of the left and right operating portions 41L and 41R are assumed to be the two treating portions 12 and 13 or 22 and 23 provided in the same manipulator 1 or 2. In contrast, the medical system according to this embodiment differs from that of the first embodiment in that it is possible to select, as the operating target of the left operating portion 41L and the operating target of the right operating portion 41R, the treating portions of the manipulators 1 and 2 that are different from each other, and that it is possible to simultaneously operate the treating portion 12 or 13 in the abdominal cavity A and the treating portion 22 or 23 in the lumen B.

In this embodiment, the abdominal-cavity manipulator 1 has a high-frequency knife 12 and forceps 13 serving as the treating portions. The lumen manipulator 2 has a high-frequency knife 22 and forceps 23 serving as the treating portions.

Figure 6:
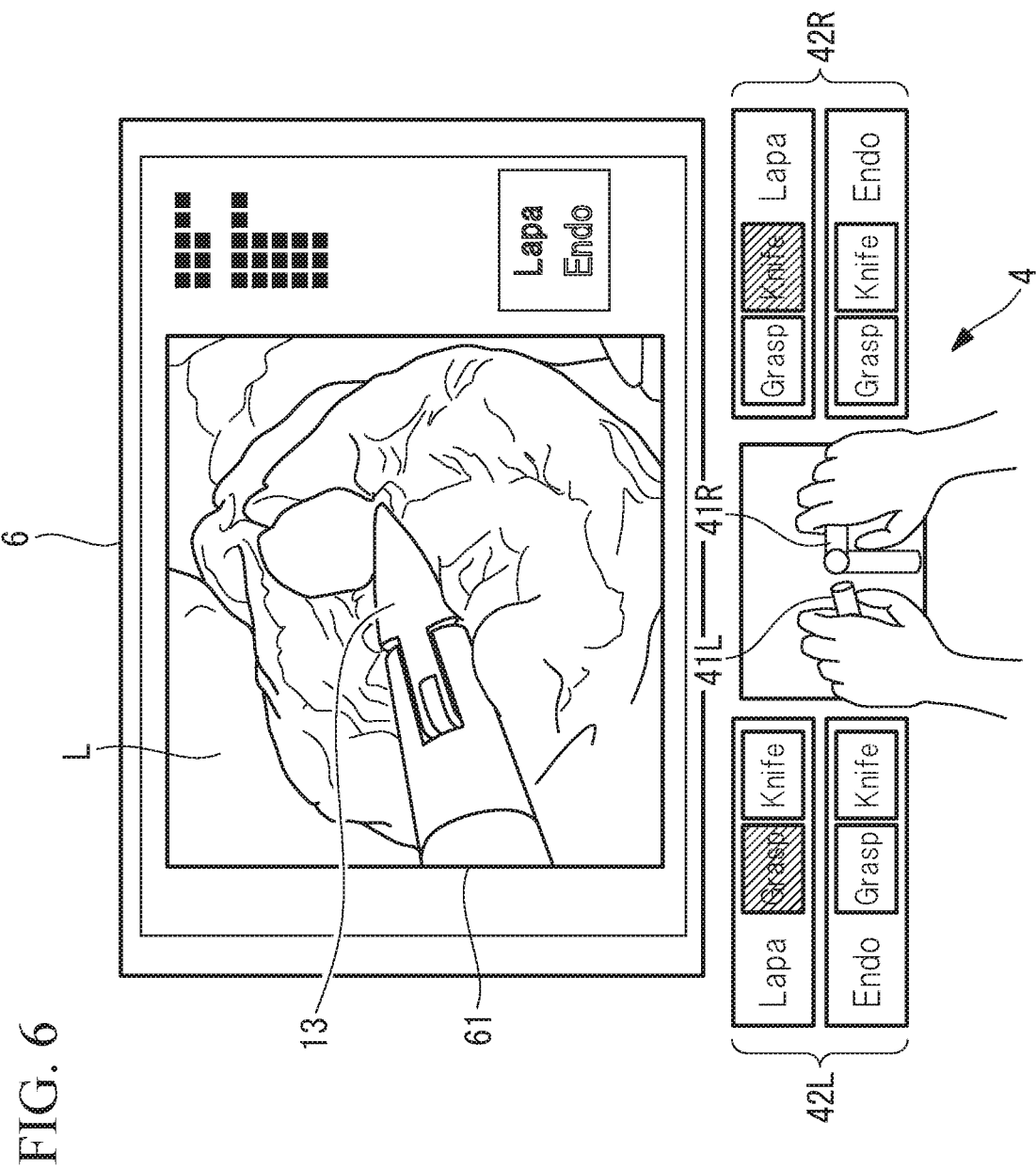
FIG. 6 is a diagram showing an interface portion and a display portion of a medical system according to a second embodiment of the present invention, and is a diagram for explaining a screen display in the case in which left and right operating targets are two treating portions in the abdominal cavity.
Figure 7:
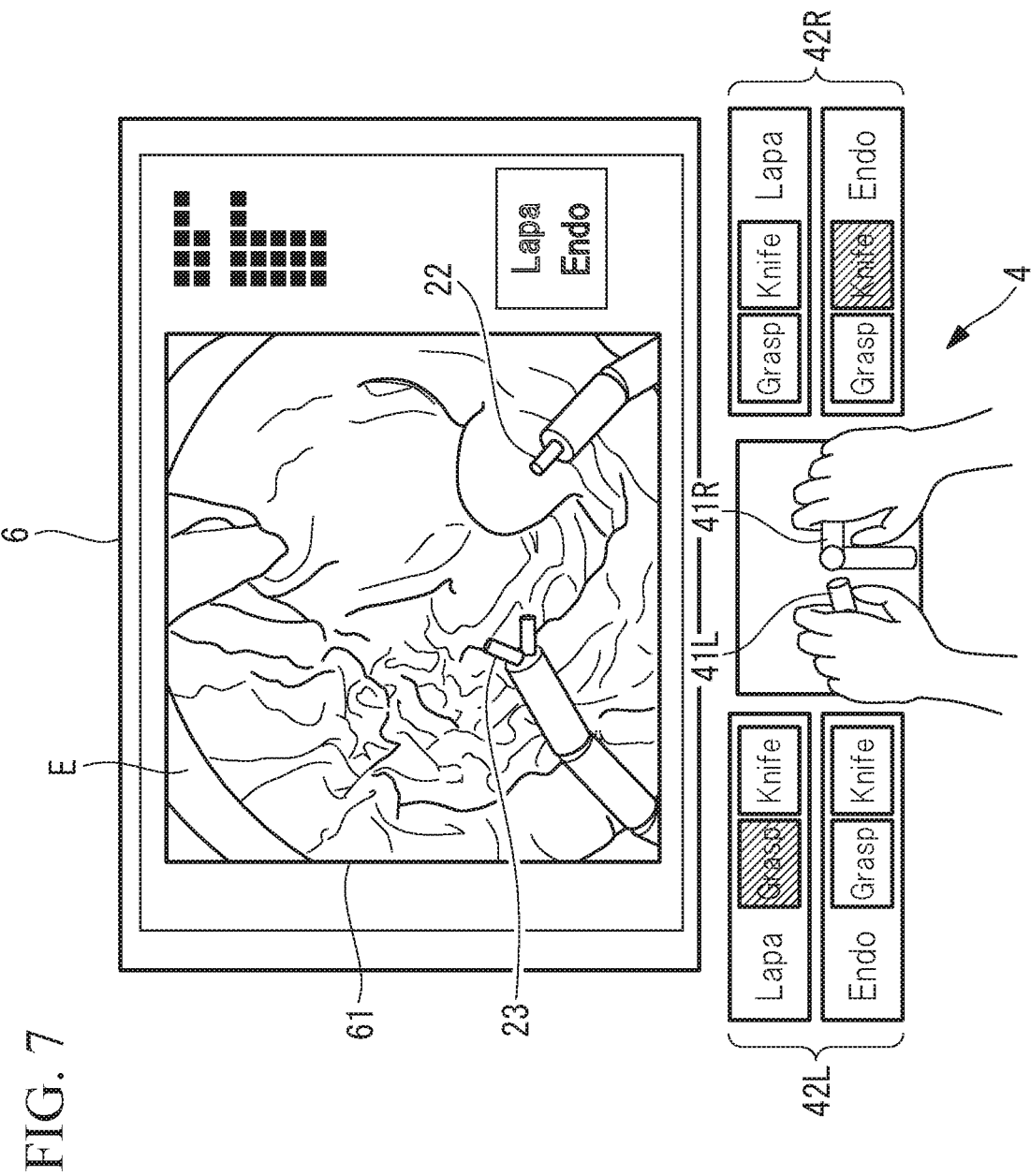
FIG. 7 is a diagram showing another example of the screen display of the medical system in FIG. 6, and is a diagram for explaining the screen display in the case in which the left operating target is forceps in the abdominal cavity and the right operating target is a high-frequency knife in the lumen.

As shown in FIGS. 6 and 7, the interface portion 4 is provided with two operating-target selecting portions 42L and 42R that correspond to the left operating portion 41L and the right operating portion 41R, respectively.

With the left operating-target selecting portion 42L, it is possible for the operator to selectively select, as the operating target (left operating target) of the left operating portion 41L, one from among "Lapa", "Endo", and, additionally, "Knife" and "Grasp". Similarly, with the right operating-target selecting portion 42R, it is possible for the operator to selectively select, as the operating target (right operating target) of the right operating portion 41R, one from among "Lapa", "Endo", and, additionally, "Knife" and "Grasp". "Knife" indicates the high-frequency knife 12 or 22 provided in the manipulators 1 or 2. "Grasp" indicates the forceps 13 or 23 provided in the manipulators 1 or 2. Therefore, the operator selects, as the left operating target, one of the four treating portions 12, 13, 22, and 23, and selects, as the right operating target, one of the four treating portions 12, 13, 22, and 23.

The left operating-target selecting portion 42L transmits information about the left operating target selected by the operator (left treating-portion selection information) to the control portion 7. The right operating-target selecting portion 42R transmits information about the right operating target selected by the operator (right treating-portion selection information) to the control portion 7.

Figure 8:
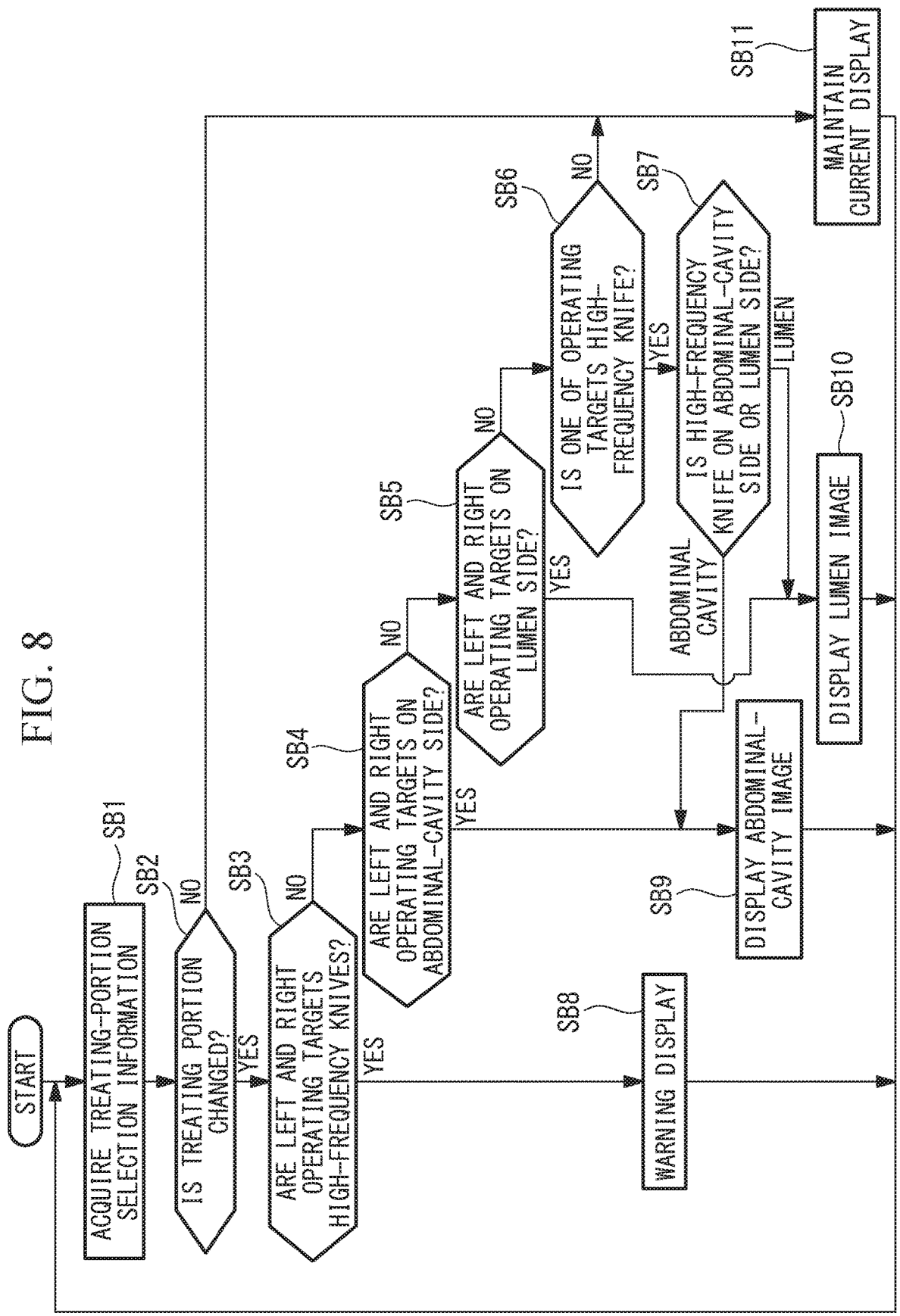
FIG. 8 is a flowchart showing a method for controlling the display in the medical system in FIG. 6.

In this embodiment, the control portion 7 controls the display on the screen 61 in accordance with the control method shown in FIG. 8.

Upon receiving the right treating-portion selection information and the left treating-portion selection information (step SB1), the control portion 7 performs the following determinations in steps SB2 to SB7 on the basis of the right treating-portion selection information and the left treating-portion selection information, and determines the image to be displayed on the screen 61.

Specifically, in the case in which there is no change in the left and right operating targets ("NO" in step SB2), the control portion 7 maintains the current display image (step SB11). On the other hand, in the case in which at least one of the operating targets is changed ("YES" in step SB2), the control portion 7 subsequently determines the combination of the left and right operating targets (steps SB3 to SB7).

In the case in which the left and right operating targets are "Knife" ("YES" in step SB3), the control portion 7 causes the screen 61 to display a warning display (step SB8). It is not desirable to use the high-frequency knives 12 and 22 in the abdominal cavity A and the lumen B at the same time. Therefore, with the warning display, the operator is prompted to reselect the left and right operating targets.

In the case in which at least one of the left and right operating targets is "Grasp" ("NO" in step SB3), the control portion 7 subsequently determines whether or not both of the operating targets are on the same side between "Lapa" and "Endo" (steps SB4 and SB5). In the case in which the left and right operating targets are "Lapa" ("YES" in step SB4), the control portion 7 selects the abdominal-cavity image L as the display image, as shown in FIG. 6, and causes the abdominal-cavity image L to be displayed on the screen 61 (step SB9). On the other hand, in the case in which the left and right operating targets are "Endo" ("YES" in step SB5), the control portion 7 selects the lumen image E as the display image, and causes the lumen image E to be displayed on the screen 61 (step SB10).

In the case in which one of the left and right operating targets is "Lapa" and the other is "Endo" ("NO" in step SB4 and "NO" in step SB5), if "Knife" is selected ("YES" in step SB6), the control portion 7 selects the display image by giving a greater priority to the image from the cavity for which "Knife" is selected, as shown in FIG. 7 ("ABDOMINAL CAVITY" or "LUMEN" in step SB7). On the other hand, in the case in which the left and right operating targets are "Grasp" ("NO" in step SB6), the control portion 7 maintains the current display image (step SB11).

The case in which the operating target is "Knife" is a case in which the operator excises the affected portion D by using the high-frequency knife 12 or 22. The image the operator needs at this time is the image in which the selected high-frequency knife 12 or 22 is captured. With this embodiment, in the case in which the left and right operating targets are the two treating portions positioned in the separate cavities A and B, the abdominal-cavity image L is given a greater priority and displayed on the screen 61 when the high-frequency knife 12 of the abdominal-cavity manipulator 1 is selected, and the lumen image E is given a greater priority and displayed on the screen 61 when the high-frequency knife 22 of the lumen manipulator 2 is selected. In this way, by determining the image the operator needs in accordance with the combination of the types of the left and right operating targets, it is possible to more effectively assist one operator to operate the two sets of treating portions 12, 13, 22, and 23 in the separate cavities A and B, and it is possible for one operator to more smoothly operate the two sets of treating portions 12, 13, 22, and 23.

Third Embodiment

Next, a medical system 300 according to a third embodiment of the present invention will be described with reference to FIGS. 9 to 12.

In this embodiment, points that differ from the first and second embodiments will mainly be described, and the configurations that are the same as those of the first and second embodiments will be given the same reference signs, and descriptions thereof will be omitted.

Figure 10:
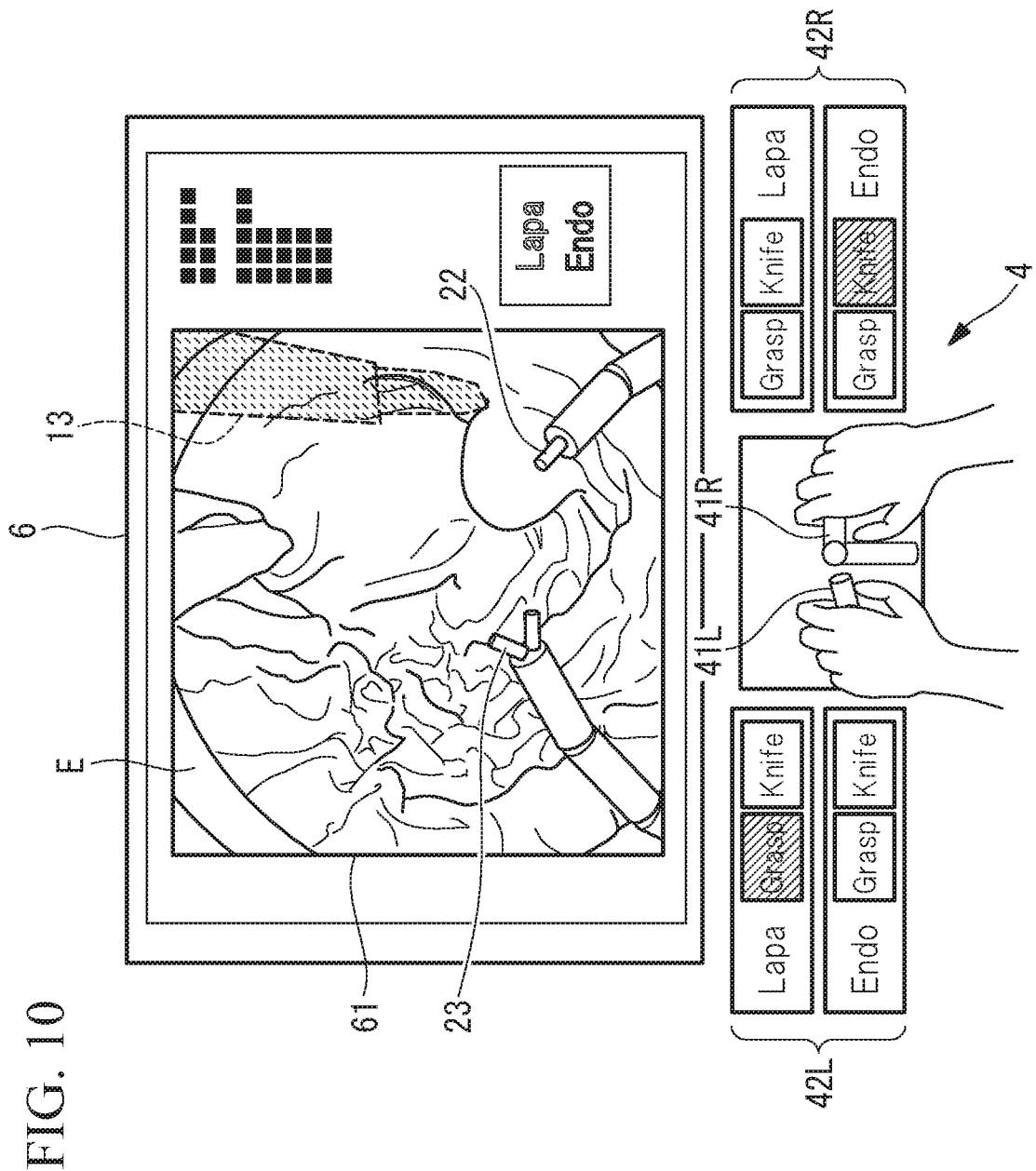
FIG. 10 is a diagram showing an interface portion and a display portion of the medical system in FIG. 9, and is a diagram for explaining a screen display in the case in which a left operating target is forceps in the abdominal cavity and a right operating target is a high-frequency knife in the lumen.

The medical system 300 according to this embodiment differs from that of the second embodiment in that, in the case in which the left and right operating targets are the treating portions positioned in the separate cavities A and B, an image of the treating portion 13 in the cavity A on the other side is displayed by being superimposed on the image E to be displayed on the screen 61, as shown in FIG. 10.

Figure 9:
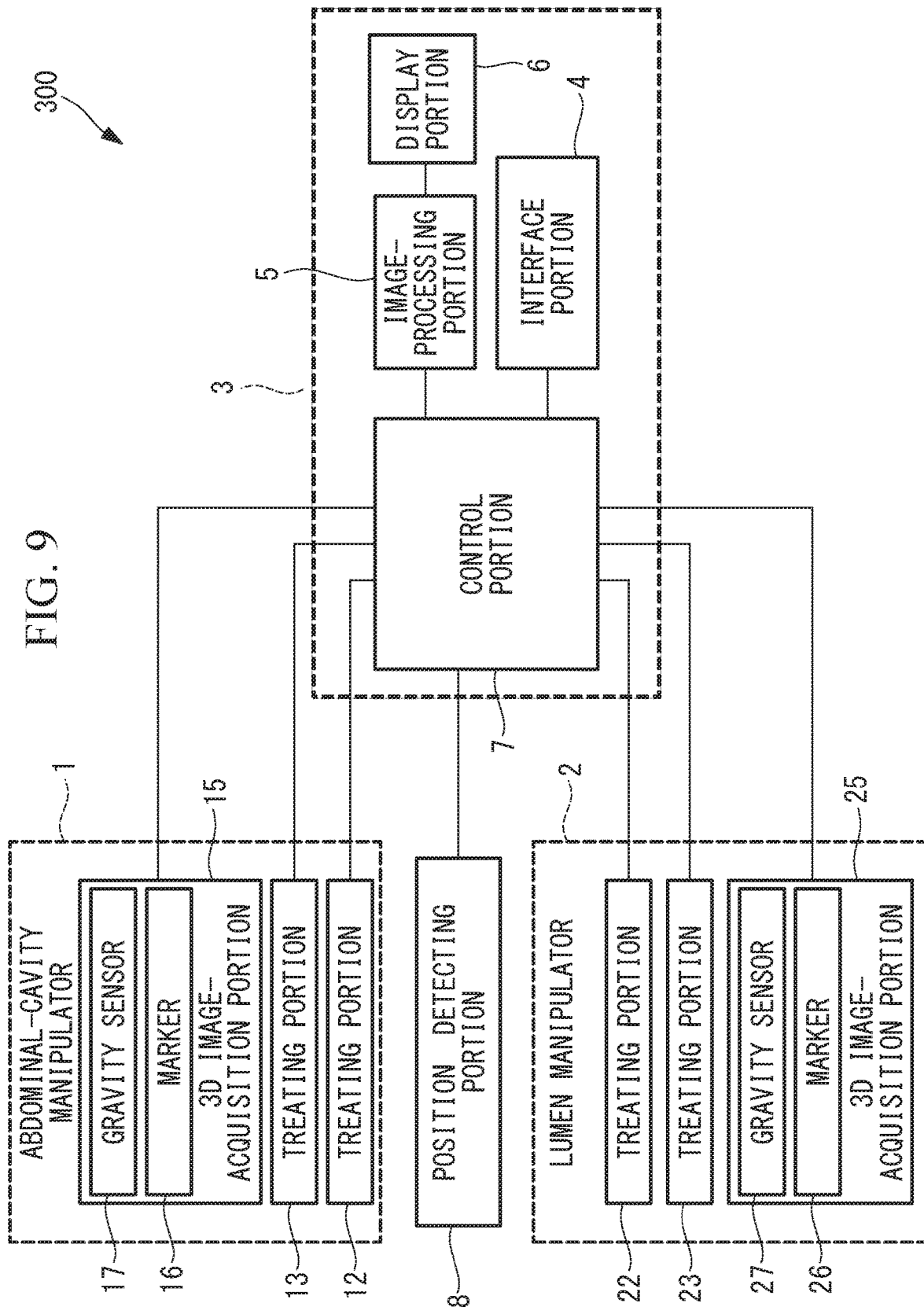
FIG. 9 is a block diagram showing the overall configuration of a medical system according to a third embodiment of the present invention.

As shown in FIG. 9, the medical system 300 is provided with 3D image-acquisition portions 15 and 25 that acquire three-dimensional (3D) images, instead of the image-acquisition portions 14 and 24, which acquire two-dimensional images. Furthermore, the medical system 300 is further provided with: a marker 16 and a gravity sensor 17 provided in the 3D image-acquisition portion 15 of the abdominal-cavity manipulator 1; a marker 26 and a gravity sensor 27 provided in the 3D image-acquisition portion 25 of the lumen manipulator 2; and a position detecting portion 8 that is disposed outside the body and that detects positions of the individual 3D image-acquisition portions 15 and 25 on the basis of signals from the individual markers 16 and 26.

The markers 16 and 26 generate signals (for example, magnetic fields) that are propagated to outside the body from inside the body.

The position detecting portion 8 receives the signals generated by the individual markers 16 and 26, detects the positions of the individual 3D image-acquisition portions 15 and 25 on the basis of the received signals, and transmits the detected positions of the 3D image-acquisition portions 15 and 25 to the control portion 7.

The gravity sensors 17 and 27 individually detect the orientations of the 3D image-acquisition portions 15 and 25 in three axial directions that are orthogonal to each other, and transmit the detected orientations of the 3D image-acquisition portions 15 and 25 to the control portion 7.

Figure 11:
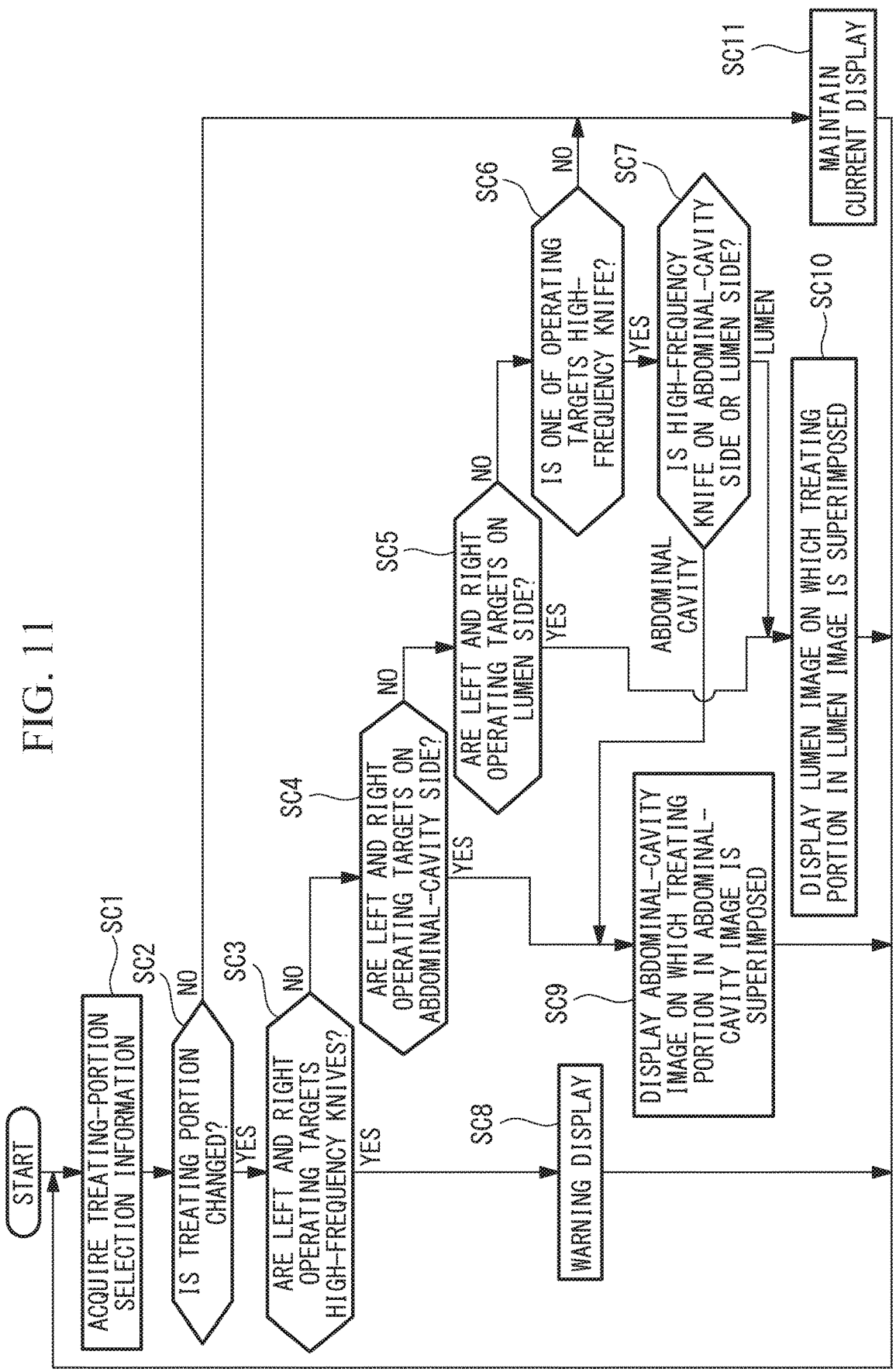
FIG. 11 is a flowchart showing a method for controlling the display in the medical system in FIG. 9.

In this embodiment, the control portion 7 controls the display on the screen 61 in accordance with the control method shown in FIG. 11.

Steps SC1 to SC8 and SC11 are the same as steps SB1 to SB8 and SB11 of the second embodiment, respectively.

In the case in which the abdominal-cavity image L is selected as the display image, the control portion 7 causes the image-processing portion (superimposing processing portion) 5 to generate a superimposed image in which the treating portions 22 and 23 in the lumen image E are superimposed on the abdominal-cavity image L, and causes the superimposed image to be displayed on the screen 61 (step SC9). On the other hand, in the case in which the lumen image E is selected as the display image, the control portion 7 causes the image-processing portion 5 to generate a superimposed image in which the treating portions 12 and 13 in the abdominal-cavity image L are superimposed on the lumen image E, and causes the superimposed image to be displayed on the screen 61 (step SC10).

Figure 12:
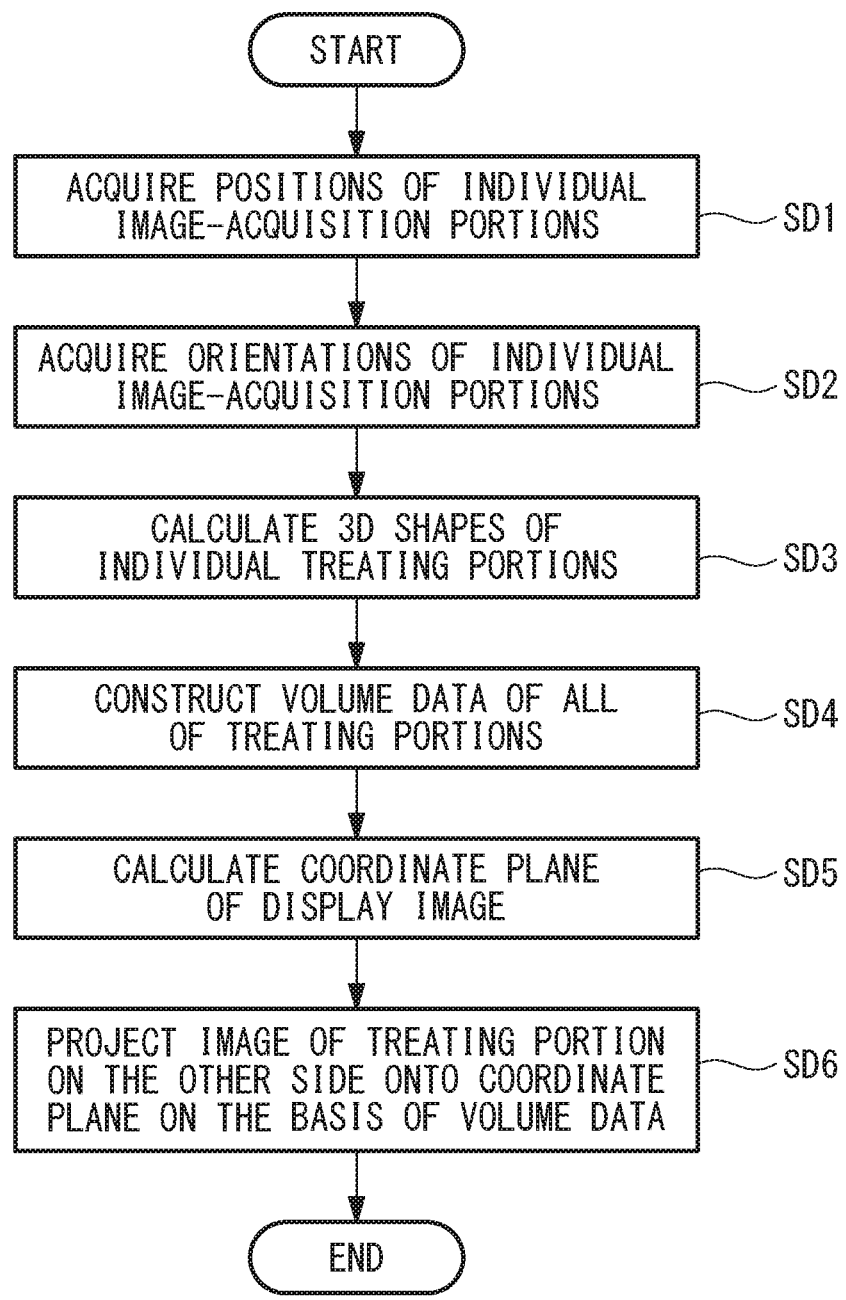
FIG. 12 is a flowchart showing a method for generating a superimposed image in the medical system in FIG. 9.

FIG. 12 shows a method for generating the superimposed images in steps SC9 and SC10.

As shown in FIG. 12, the control portion 7 causes the position detecting portion 8 to detect the positions of the individual image-acquisition portions 15 and 25, and acquires the positional coordinates of the individual image-acquisition portions 15 and 25 from the position detecting portion 8 (step SD1). In addition, the control portion 7 causes the individual gravity sensors 17 and 27 to detect the orientations of the individual image-acquisition portions 15 and 25, and acquires information about the orientations of the individual image-acquisition portions 15 and 25 from the gravity sensors 17 and 27 (step SD2). In addition, the control portion 7 calculates 3D shapes of the individual treating portions 12, 13, 22, and 23 from 3D image signal information received from the individual image-acquisition portions 15 and 25 (step SD3). The control portion 7 transmits, to the image-processing portion 5, the positional coordinates and the information about the orientations of the individual image-acquisition portions 15 and 25, and the 3D shapes of the individual treating portions 12, 13, 22, and 23 that are obtained in steps SD1 to SD3.

Next, the image-processing portion 5, on the basis of the information and the data received from the control portion 7, constructs volume data for all of the treating portions 12, 13, 22, and 23 (step SD4). In order to construct the volume data, angles of view of the individual image-acquisition portions 15 and 25, information about relative positions of the image-acquisition portion 15 and the treating portions 12 and 13, and information about relative positions of the image-acquisition portion 25 and the treating portions 22 and 23 are additionally employed. The angles of view and the information about the relative positions are held in the image-processing portion 5 in advance.

Next, image-processing portion 5 calculates the coordinate plane of the display image on the basis of the orientations of the image-acquisition portion 15 or 25 and the angle of view thereof corresponding to the display image (step SD5). Next, by using the volume data, the image-processing portion 5 projects, onto the coordinate plane, the data of the treating portion (on the other side) corresponding to the image that is not the display image (step SD6). By doing so, the superimposed image is generated.

Note that the 3D shapes of the individual treating portions 12, 13, 22, and 23 may be calculated by the control portion 7 by means of computations performed on the basis of the control information of the manipulators 1 and 2 and design data of the individual treating portions.

As has been described above, with this embodiment, in the case in which the operator simultaneously operates the treating portions 12 and 13 in the abdominal cavity A and the treating portions 22 and 23 in the lumen B, the treating portions 12 and 13 in the abdominal cavity A are superimposed on the lumen image E if the display image is the lumen image E, and the treating portions 22 and 23 in the lumen B are superimposed on the abdominal-cavity image L if the display image is the abdominal-cavity image L. Therefore, it is possible for the operator to also ascertain the states of the treating portions positioned on the other side of the wall C from the display image. By doing so, it is possible to more effectively assist one operator to operate the two sets of treating portions 12, 13, 22, and 23 in the separate cavities A and B, and it is possible for one operator to more smoothly operate the two sets of treating portions 12, 13, 22, and 23.

Fourth Embodiment

Next, a medical system according to a fourth embodiment of the present invention will be described with reference to FIGS. 13 to 15.

In this embodiment, points that differ from the first and second embodiments will mainly be described, and the configurations that are the same as those of the first and second embodiments will be given the same reference signs, and descriptions thereof will be omitted.

Figure 13:
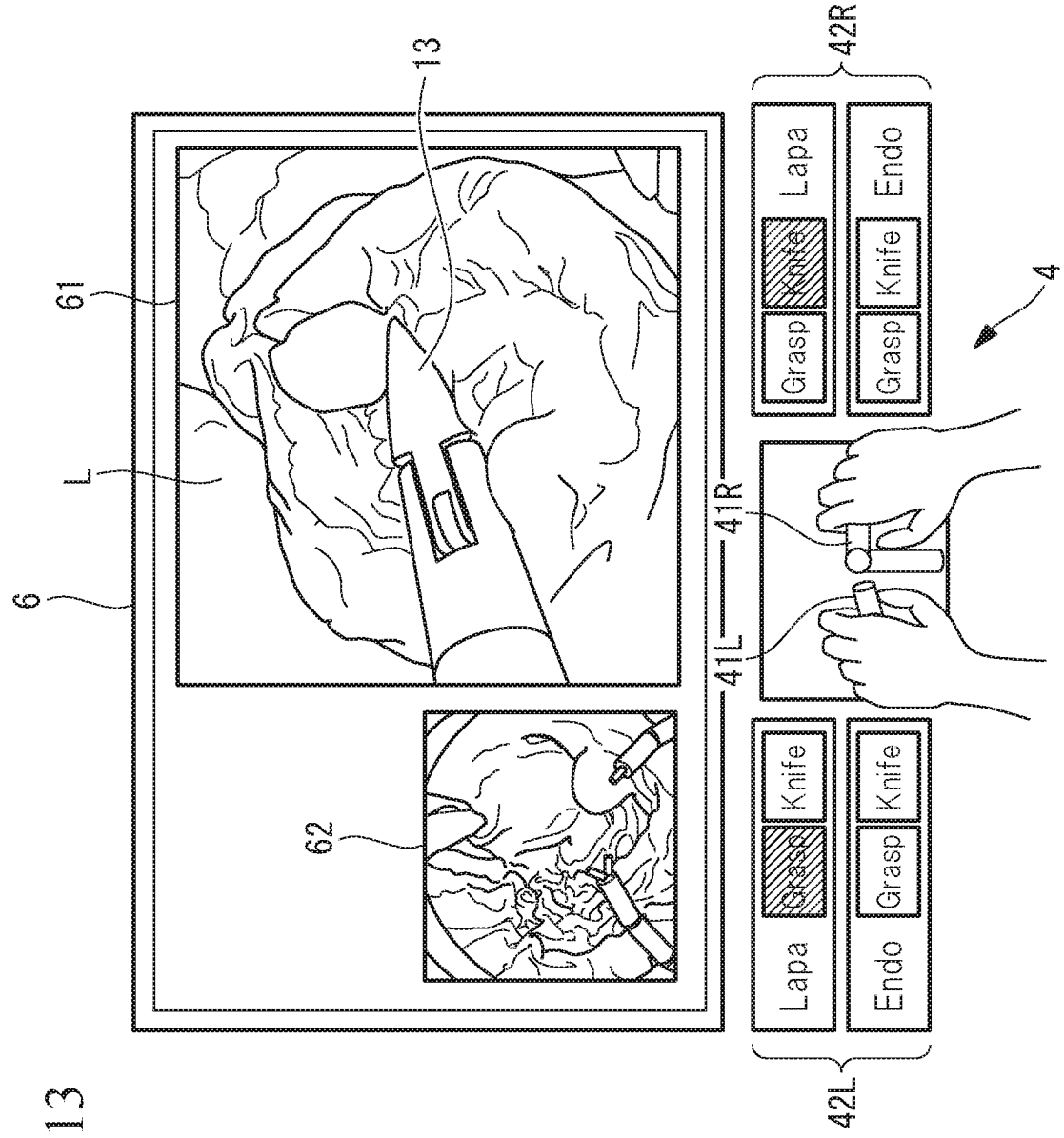
FIG. 13 is a diagram showing an interface portion and a display portion of a medical system according to a fourth embodiment of the present invention, and is a diagram for explaining a screen display in the case in which left and right operating targets are treating portions in the abdominal cavity.
Figure 14:
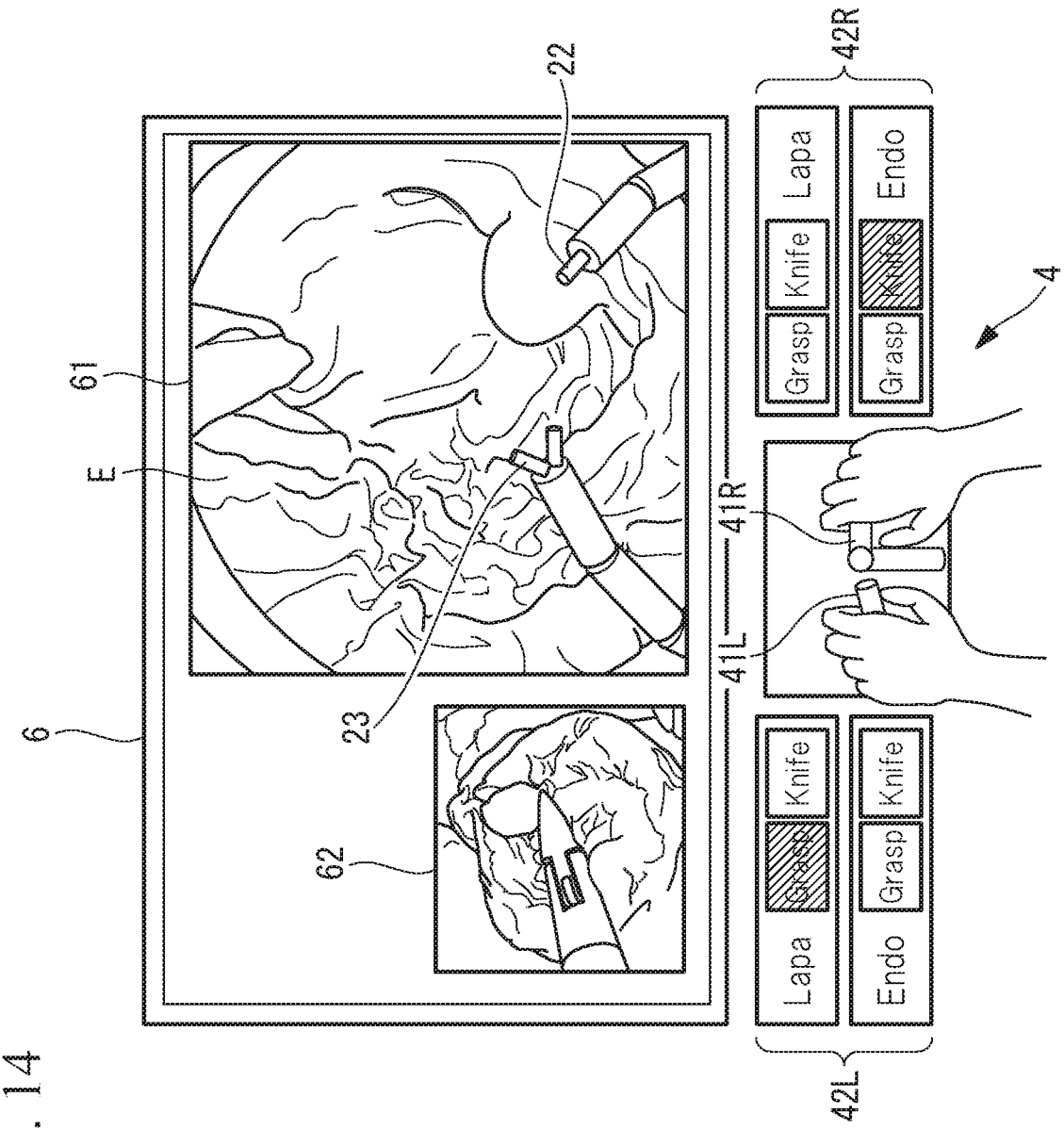
FIG. 14 is a diagram showing another example of the screen display of the medical system in FIG. 13, and is a diagram for explaining the screen display in the case in which the left operating target is forceps in the abdominal cavity and the right operating target is a high-frequency knife in the lumen.

As shown in FIGS. 13 and 14, the medical system according to this embodiment differs from that of the second embodiment in that the display portion 6 has a sub-screen 62 that is provided next to the screen (hereinafter referred to as a main screen) 61 and that displays an image that is not the display image. The sub-screen 62 has smaller dimensions than those of the main screen 61.

Figure 15:
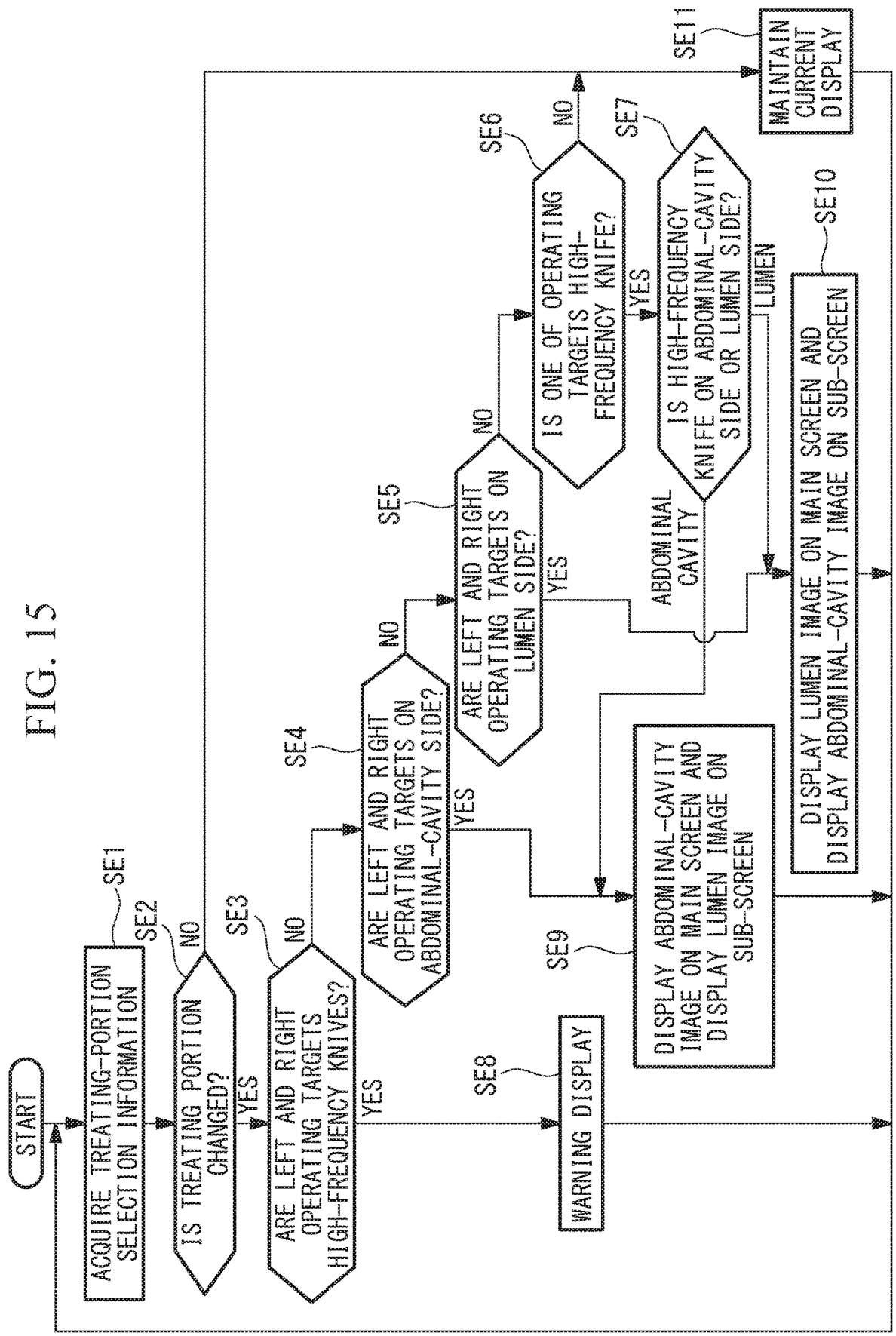
FIG. 15 is a flowchart for explaining a method for controlling the display in the medical system in FIG. 13.

In this embodiment, the control portion 7 controls the displays of the main screen 61 and the sub-screen 62 in accordance with the control method shown in FIG. 15.

Steps SE1 to SE8 and SE11 are the same as steps SB1 to SB8 and SB11 of the second embodiment, respectively.

In the case in which the abdominal-cavity image L is selected as the display image, the control portion 7 causes the abdominal-cavity image L to be displayed on the main screen 61, as shown in FIG. 13, and causes the lumen image E to be displayed on the sub-screen 62 (step SE9). On the other hand, in the case in which the lumen image E is selected as the display image, the control portion 7 causes the lumen image E to be displayed on the main screen 61, as shown in FIG. 14, and causes the abdominal-cavity image L to be displayed on the sub-screen 62 (step SE10).

As has been described above, in this embodiment, because the image L or E that is not the display image E or L is displayed on the sub-screen 62, it is possible for the operator to more accurately ascertain the states of the treating portions 12, 13, 23, and 22 in both the abdominal cavity A and the lumen B. By doing so, it is possible to more effectively assist one operator to operate the two sets of treating portions 12, 13, 22, and 23 in the separate cavities A and B, and it is possible for one operator to more smoothly operate the two sets of treating portions 12, 13, 22, and 23.

In this embodiment, the superimposed image described in the third embodiment may be displayed on the main screen 61. Furthermore, a superimposed image (sub-superimposed image) may also be displayed on the sub-screen 62. In this case, the image-processing portion 5 generates, by using a method that is similar to that in steps SD5 and SD6, a superimposed image in which the treating portions in the cavity that is the same as that in the display image are superimposed on the image that is not the display image.

By doing so, it is possible for the operator to more accurately ascertain the states of the treating portions 12, 13, 23, and 22 in both the abdominal cavity A and the lumen B on the basis of the superimposed images displayed on the main screen 61 and the sub-screen 62.

Fifth Embodiment

Next, a medical system according to a fifth embodiment of the present invention will be described with reference to FIGS. 16 to 18B.

In this embodiment, points that differ from the first and second embodiments will mainly be described, and the configurations that are the same as those of the first and second embodiments will be given the same reference signs, and descriptions thereof will be omitted.

The medical system according to this embodiment differs from that of the second embodiment in that the display image is rotated so that the motion directions of the treating portions in the display image on the main screen 61 correspond to the operation directions of the operating portions 41L and 41R. Although FIGS. 16 and 17 show an example in which the sub-screen 62 described in the fourth embodiment is provided in the display portion 6, the sub-screen 62 need not be provided in the display portion 6, as in the second embodiment.

Figure 16:
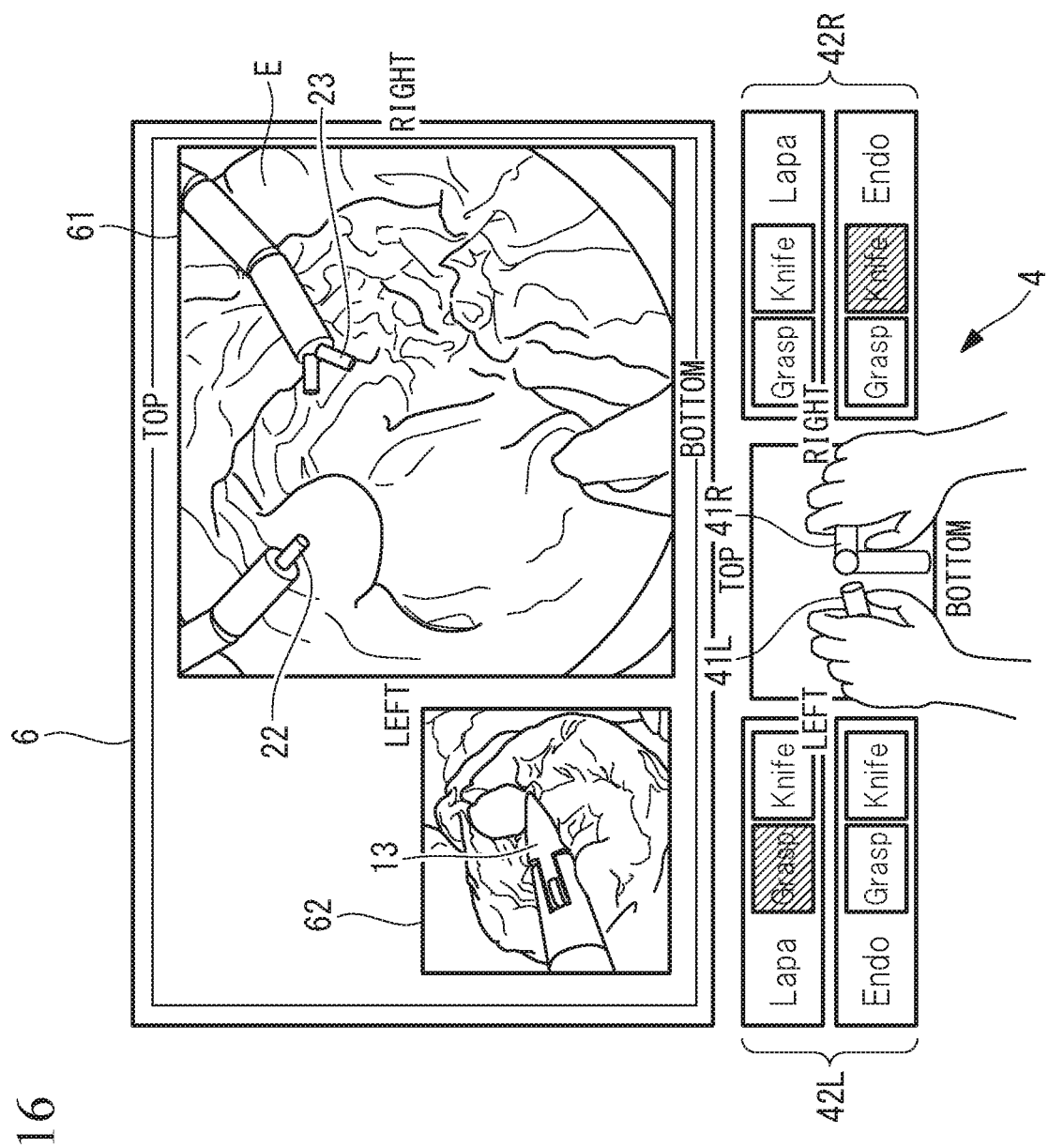
FIG. 16 is a diagram showing an interface portion and a display portion of a medical system according to a fifth embodiment of the present invention.
Figure 17:
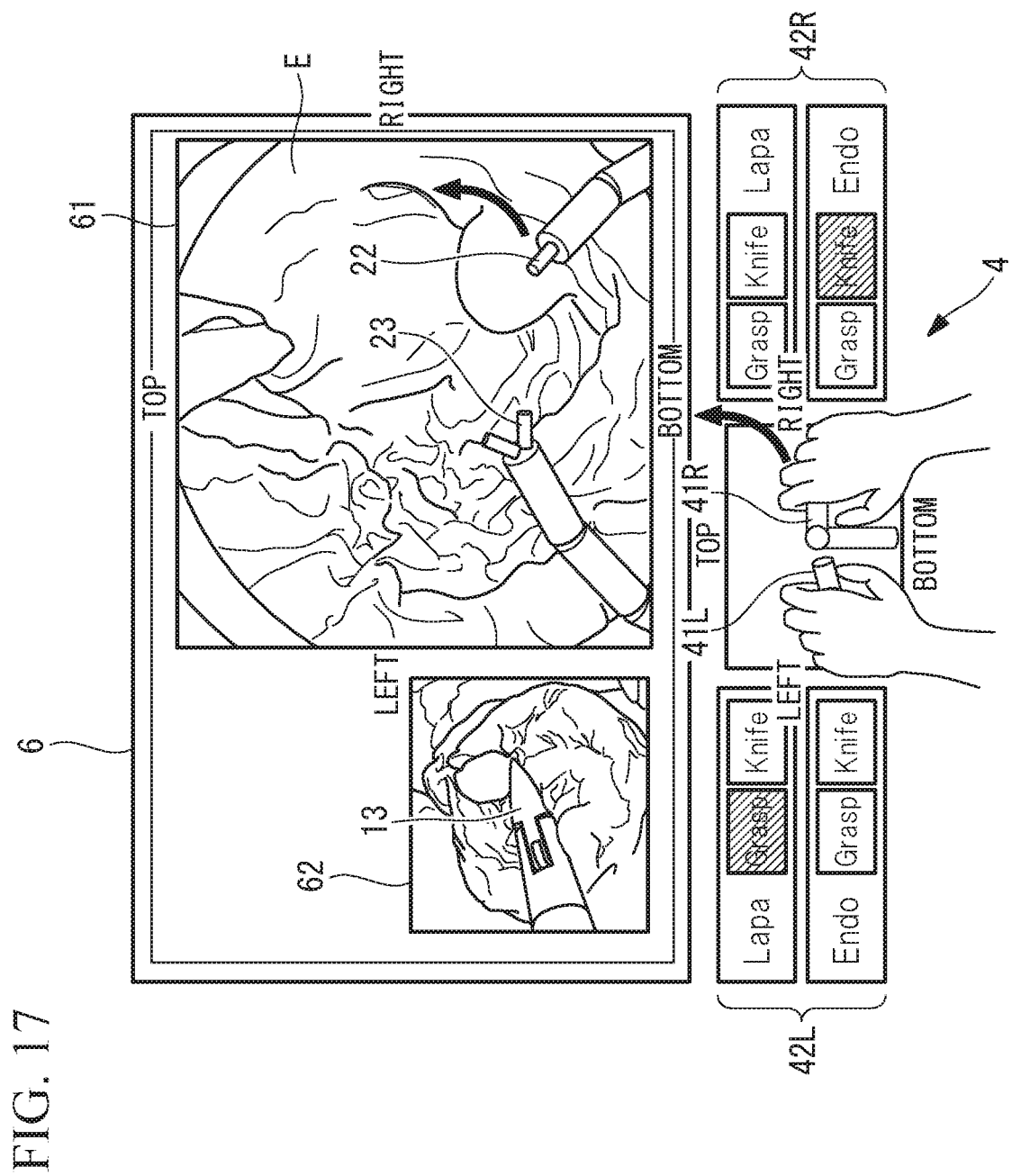
FIG. 17 is a diagram for explaining the screen display in FIG. 16 after a display image on a main screen has been rotated.

As shown in FIGS. 16 and 17, the main screen 61 and the operating portions 41L and 41R have top, bottom, left, and right directions, respectively. The top, bottom, left, and right directions of the main screen 61 and the top, bottom, left, and right directions of the operating portions 41L and 41R correspond to each other.

Figure 18A:
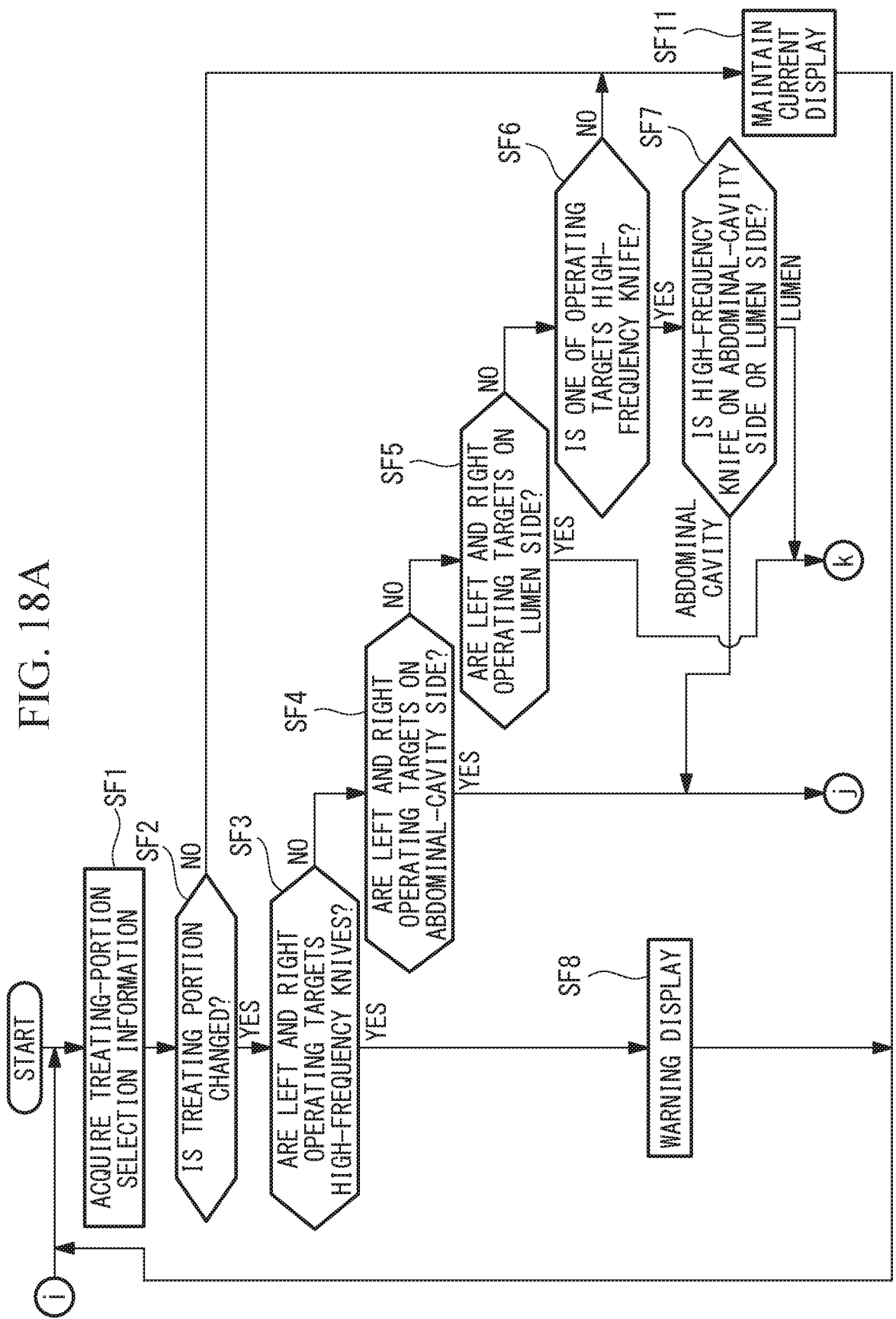
FIG. 18A is a flowchart showing a method for controlling the display in the medical system in FIG. 16.
Figure 18B:
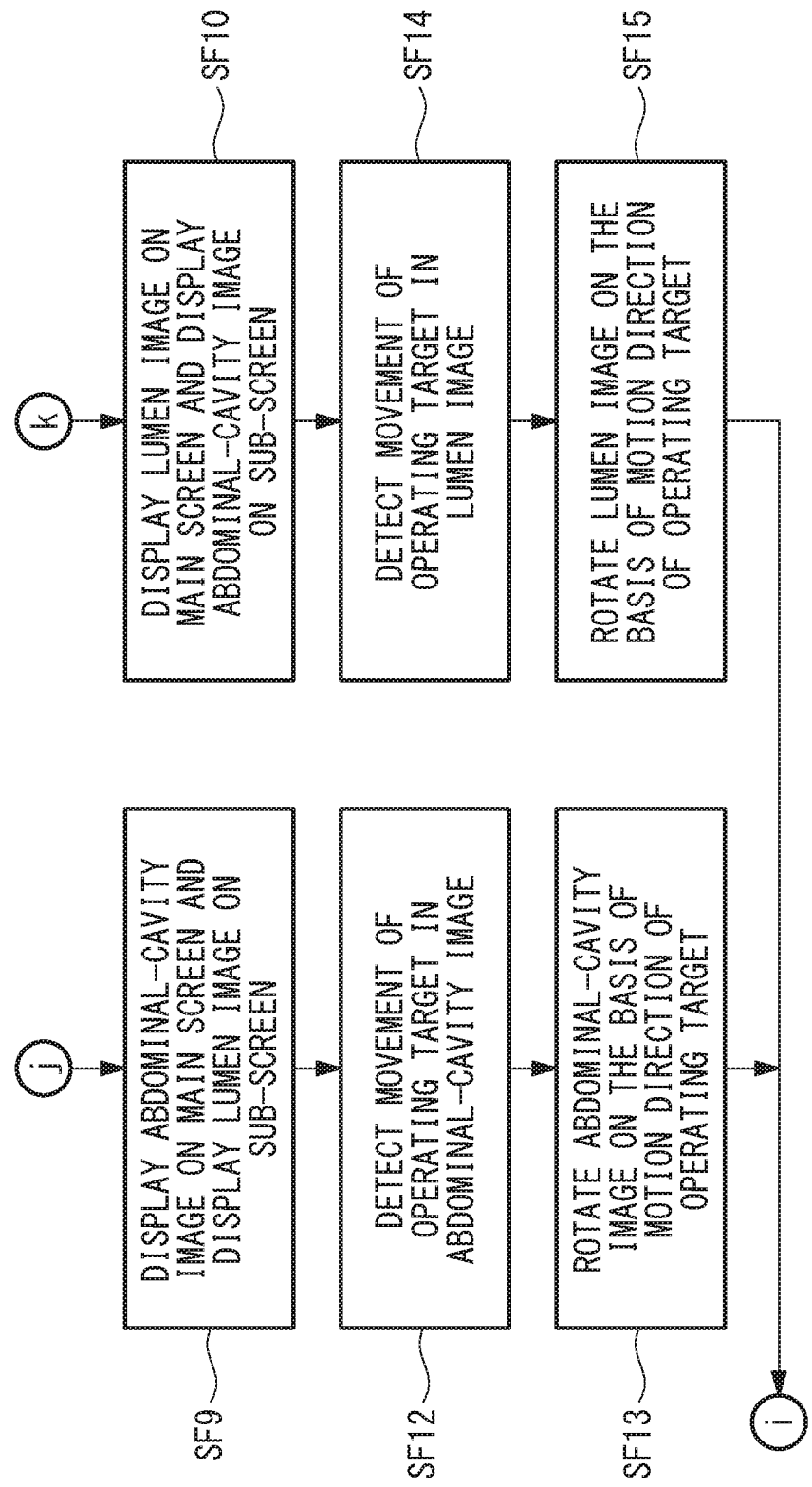
FIG. 18B is a flowchart showing a continuation of FIG. 18A

In this embodiment, the control portion 7 controls the rotation of the display image on the main screen 61 in accordance with the control method shown in FIGS. 18A and 18B.

Steps SF1 to SF11 are the same as steps SE1 to SE11 of the fourth embodiment, respectively.

As shown in FIG. 16, after causing the lumen image E to be displayed on the main screen 61 in step SF10, when the treating portions 22 and 23 in the lumen image E are moved as a result of the operator operating the operating portions 41L and 41R, the control portion 7 detects the motion directions of the treating portions 22 and 23 in the lumen image E (step SF14). Then, the control portion 7 calculates the rotational angles of the lumen image E so that the motion directions of the treating portions 22 and 23 on the main screen 61 (in the coordinate system of the main screen 61) correspond to the operation directions of the operating portions 41L and 41R. Next, the control portion 7 controls the image-processing portion (rotating processing portion) 5 so as to rotate the lumen image E by an amount corresponding to the calculated rotational angle (step SF15). By doing so, as shown in FIG. 17, the lumen image E on the main screen 61 is rotated so that the operation directions of the operating portions 41L and 41R and the motion directions of the treating portions 22 and 23 on the main screen 61 coincide with each other.

Similarly, after causing the abdominal-cavity image L to be displayed on the main screen 61 in step SF9, when the treating portions 12 and 13 in the abdominal-cavity image L are moved as a result of the operator operating the operating portions 41L and 41R, the control portion 7 detects motion directions of the treating portions 12 and 13 in the abdominal-cavity image L (step SF12). Then, the control portion 7 calculates the rotational angle of the abdominal-cavity image L so that the motion directions of the treating portions 12 and 13 on the main screen 61 (in the coordinate system of the main screen 61) correspond to the operation directions of the operating portions 41L and 41R. Next, the control portion 7 controls the image-processing portion 5 so as to rotate the abdominal-cavity image L by an amount corresponding to the calculated rotational angle (step SF13). By doing so, the abdominal-cavity image L on the main screen 61 is rotated so that the operation directions of the operating portions 41L and 41R and the motion directions of the treating portions 12 and 13 on the main screen 61 coincide with each other.

Depending on the orientations of the manipulators 1 and 2 inside the body, displacement occurs between the top, bottom, left, and right directions of the treating portions 12, 13, 22, and 23 and the top, bottom, left, and right directions of the operating portions 41L and 41R. When the operating portions 41L and 41R are operated in the state in which the top, bottom, left, and right directions of the treating portions 12, 13, 22, and 23 and the top, bottom, left, and right directions of the operating portions 41L and 41R are displaced from each other, the treating portions 12, 13, 22, and 23 are moved on the main screen 61 in directions that are different from the operation directions of the operating portions 41L and 41R. Therefore, as shown in FIG. 17, by rotating the display image so that the operation directions of the operating portions 41L and 41R and the motion directions of the treating portions 12 and 13 or 22 and 23 on the main screen 61 coincides each other, it is possible for the operator to more intuitively operate the treating portions 12, 13, 22, and 23 by using the operating portions 41L and 41R.

Sixth Embodiment

Next, a medical system according to a sixth embodiment of the present invention will be described with reference to FIGS. 19 to 24.

In this embodiment, points that differ from the second embodiment will mainly be described, and the configurations that are the same as those of the second embodiment will be given the same reference signs, and descriptions thereof will be omitted.

As shown in FIGS. 19 to 22, the medical system according to this embodiment differs from that of the second embodiment in that the interface portion 4 is provided with a rotational operating portion 43 for rotating the display image to be displayed on the screen 61. Although FIGS. 19 to 22 show the display portion 6 that does not have the sub-screen 62, the sub-screen 62 may be provided in the display portion 6, as in the fourth embodiment.

The rotational operating portion 43 is configured so as to be rotationally operated by the operator by an arbitrary angle. The rotational operating portion 43 transmits, to the control portion 7, rotational-operation information that indicates the rotational angle of the rotational operation performed by the operator.

Figure 23A:
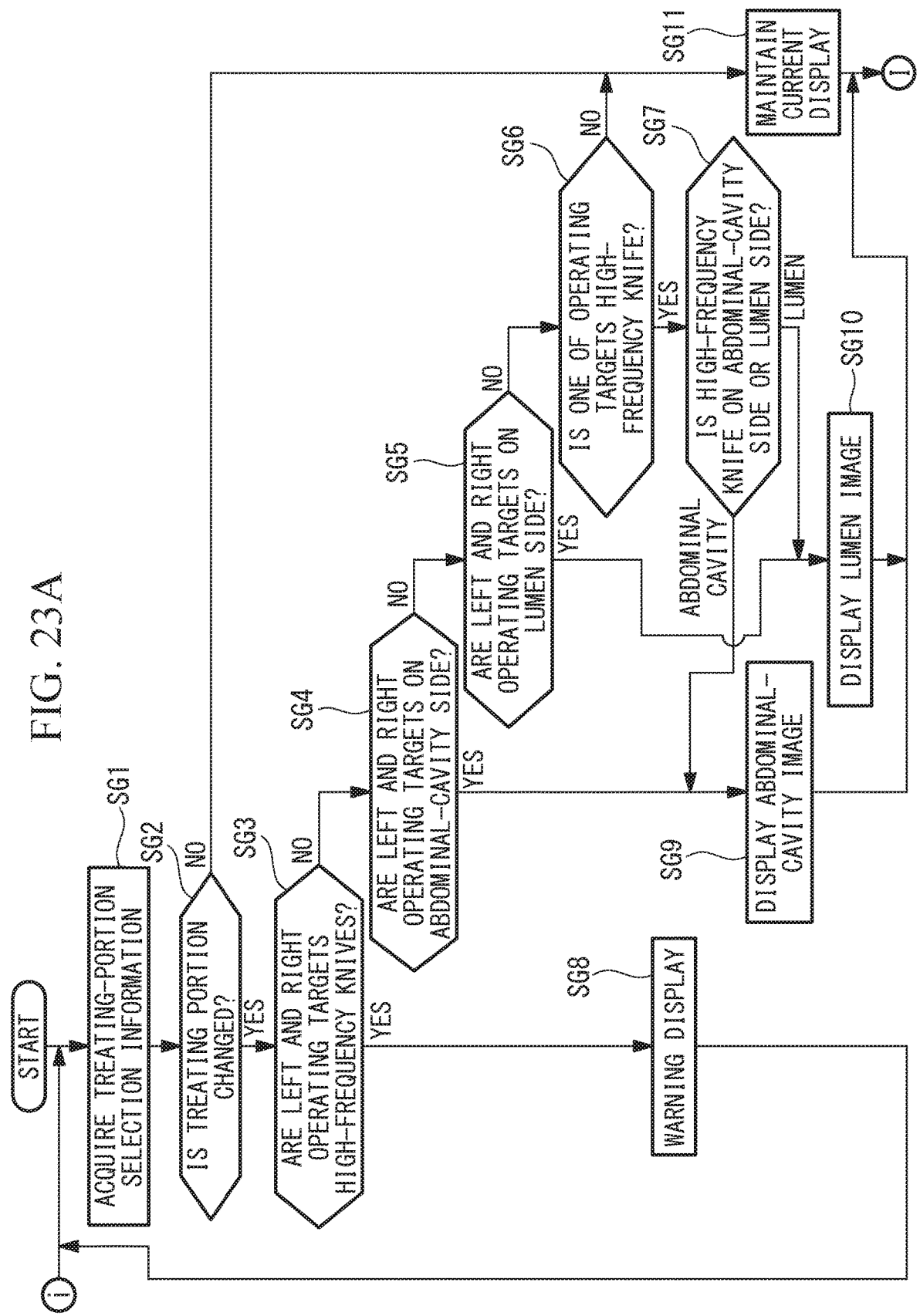
FIG. 23A is a flowchart showing a method for controlling the display in the medical system in FIG. 19.
Figure 23B:
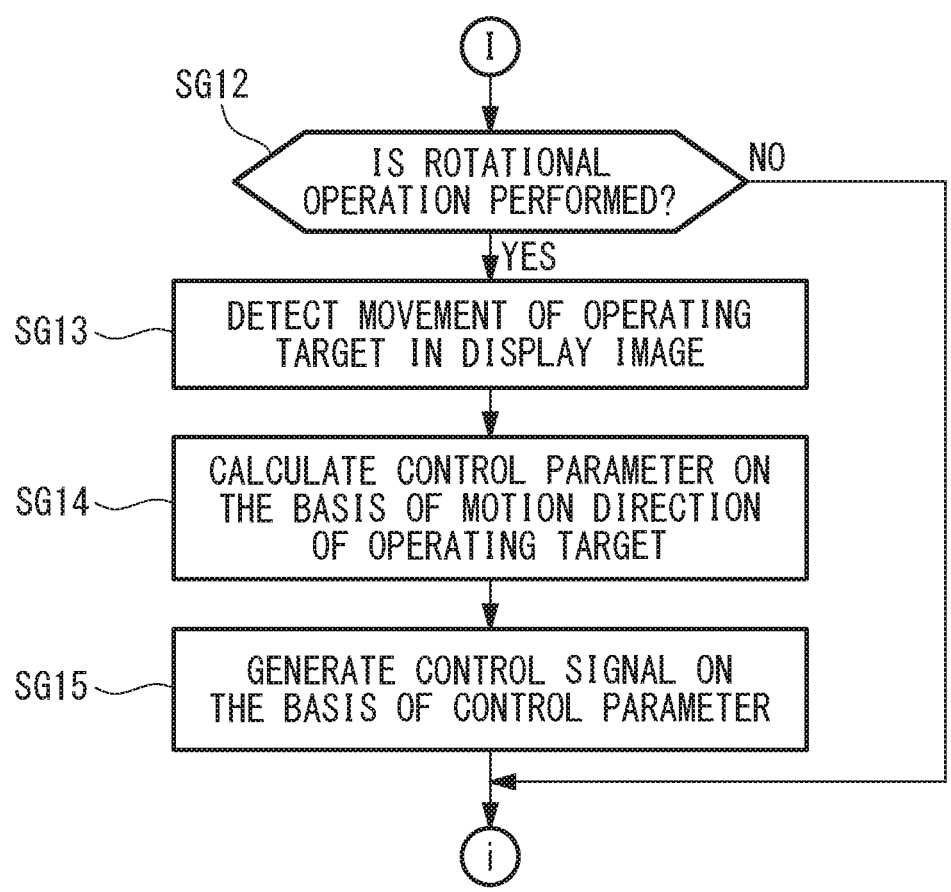
FIG. 23B is a flowchart showing a continuation of FIG. 23A.

In this embodiment, the control portion 7 controls the display of the screen 61 and the motions of the treating portions 12, 13, 22, and 23 in accordance with the control method shown in FIGS. 23A and 23B.

Figure 19:
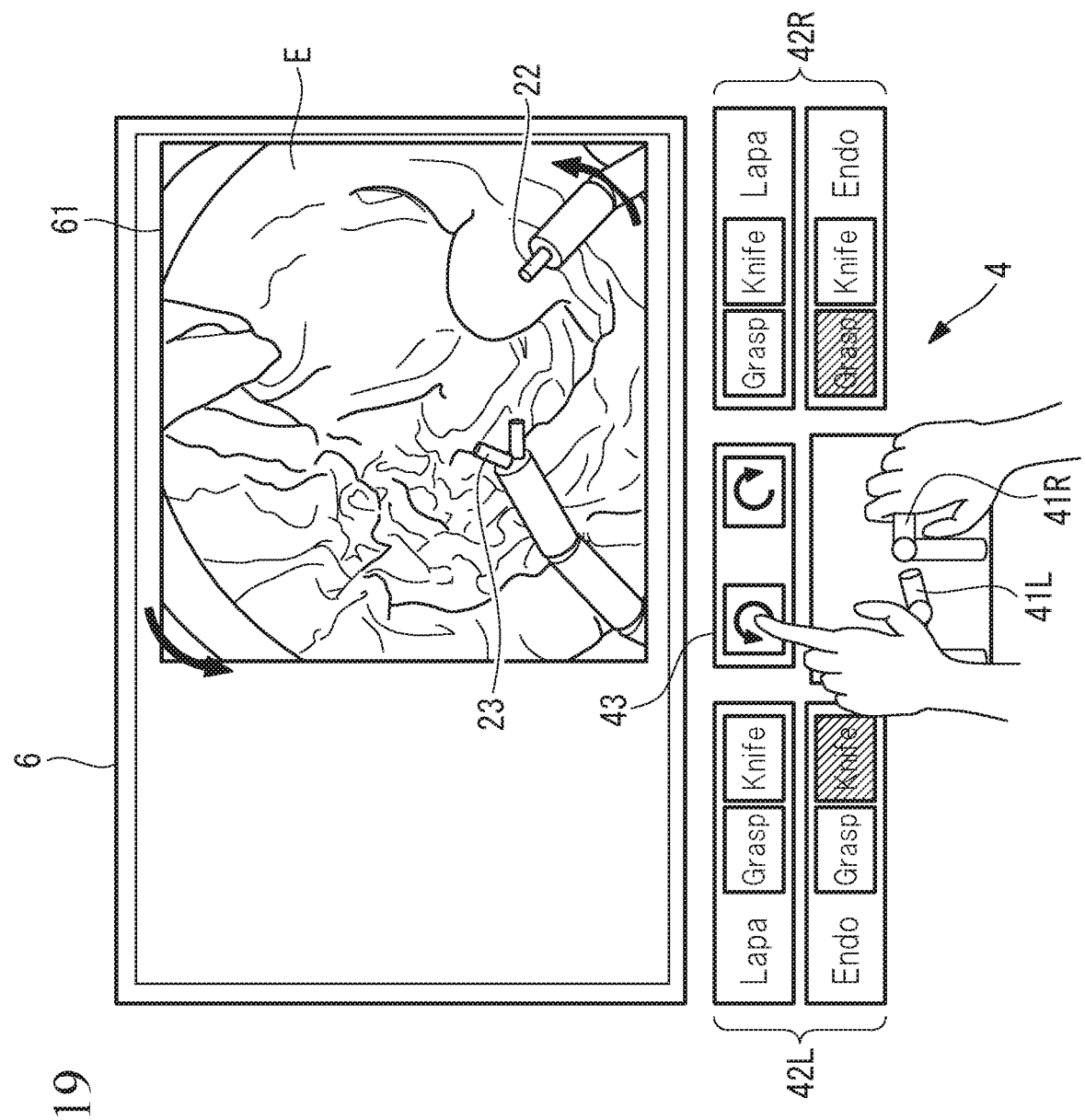
FIG. 19 is a diagram showing an interface portion and a display portion of a medical system according to a sixth embodiment of the present invention.
Figure 20:
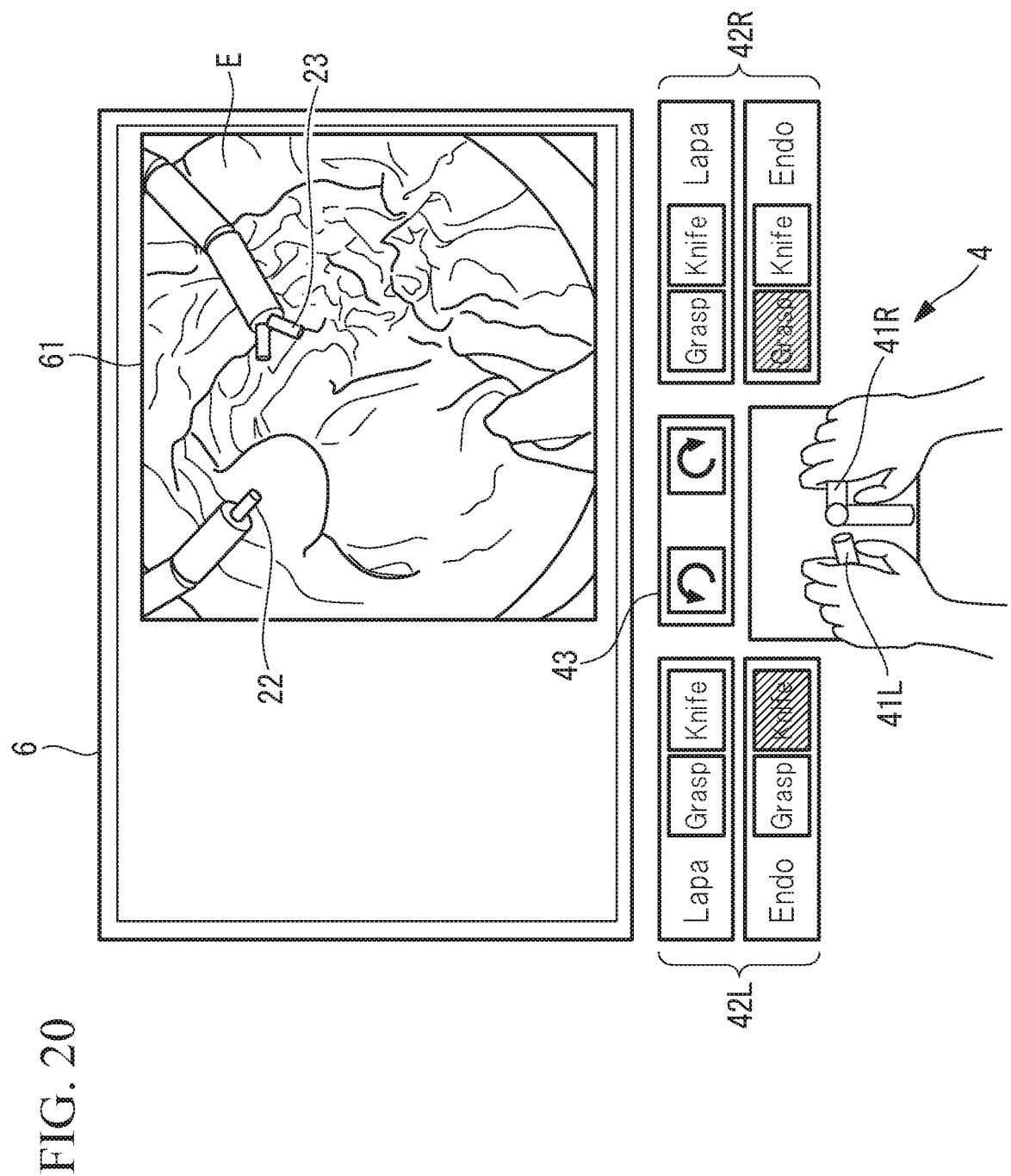
FIG. 20 is a diagram for explaining the screen display in FIG. 19 after an image on a main screen has been rotated.

Steps SG1 to SG11 are the same as steps SB1 to SB11 of the second embodiment, respectively. After causing the image E to be displayed on the screen 61, when the operator operates the rotational operating portion 43, as shown in FIG. 19, the rotating operation information is transmitted to the control portion 7 ("YES" in step SG12). The control portion 7 controls the image-processing portion (rotating processing portion) 5 so as to rotate the display image E by an amount corresponding to the rotational angle. By doing so, the display image E on the screen 61 is rotated, as shown in FIG. 20.

Figure 21:
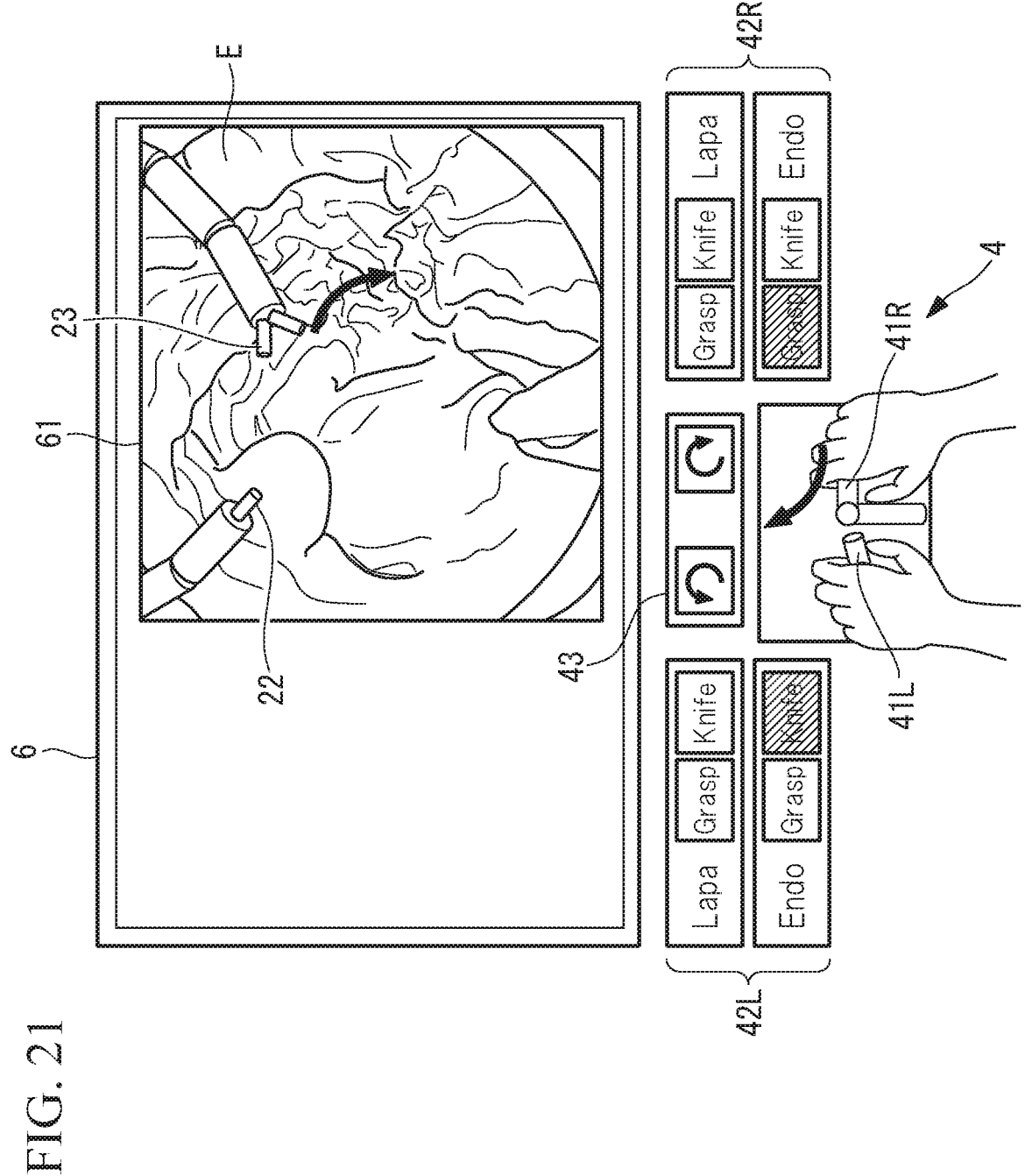
FIG. 21 is a diagram showing the relationship between the operation direction of the operating portion and the motion direction of the operating target on the screen in the screen display in FIG. 20.
Figure 22:
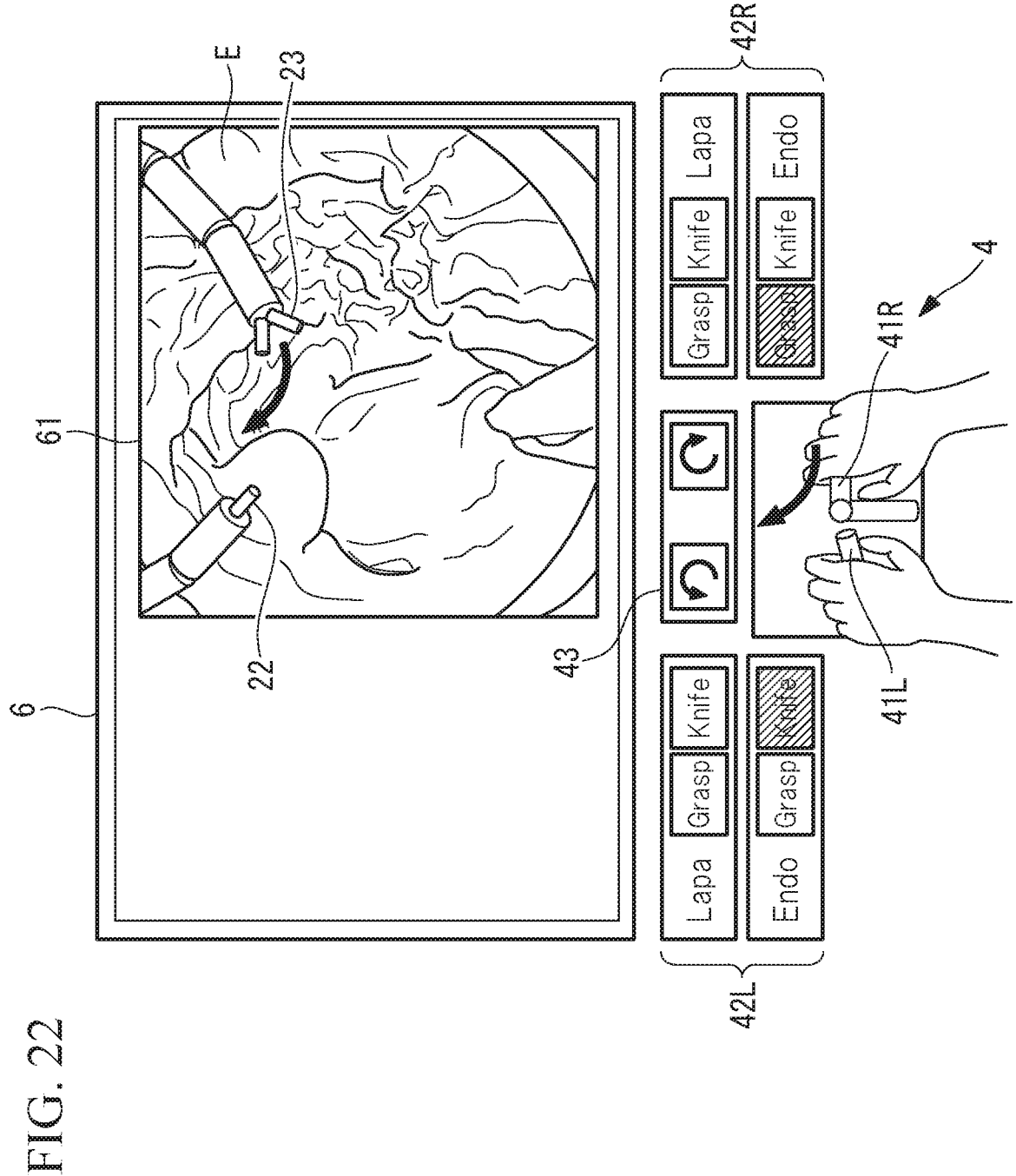
FIG. 22 is a diagram for explaining the relationship between the operation direction of the operating portion after adjusting the motion direction of the operating target and the motion direction of the operating target on the screen.

Subsequently, as shown in FIG. 21, when the treating portions 22 and 23 in the display image E are moved as a result of the operating portions 41L and 41R being operated by the operator, the control portion 7 detects the motion directions of the treating portions 22 and 23 in the display image E in a similar manner to the above-described steps SF12 and SF14 (step SG13). Next, the control portion 7 calculates control parameters for associating the motion directions of the treating portions 22 and 23 on the screen 61 with the operation directions of the operating portions 41L and 41R (step SG14), generates controls signals in which the motion directions of the treating portions 22 and 23 are adjusted by using the calculated control parameters (step SG15), and transmits the control signals to the manipulator 2. By doing so, the treating portions 22 and 23 perform motions in the directions corresponding to the operation directions of the operating portions 41L and 41R, as shown in FIG. 22.

When the operator rotates the display image E on the screen 61, a deviation may occur between the top, bottom, left, and right directions of the treating portions 22 and 23 and the top, bottom, left, and right directions of the operating portions 41L and 41R. For example, in the state in FIG. 21, when the right operating portion 41R is operated in the upper left direction, the treating portion 22 in the display image E on the screen 61 is moved in the lower right direction. Therefore, as shown in FIG. 22, by adjusting the control signals so that the operation directions of the operating portions 41L and 41R and the motion directions of the treating portions 22 and 23 on the screen 61 coincide with each other, it is possible for the operator to more intuitively operate the treating portions 22 and 23 by using the operating portions 41L and 41R.

Figure 24:
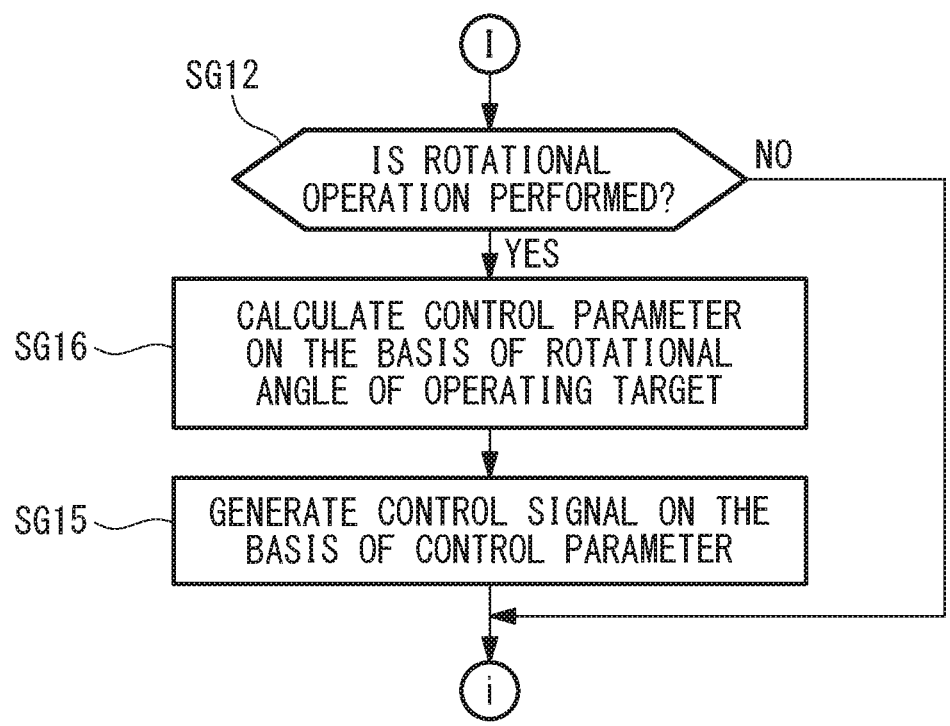
FIG. 24 is a flowchart showing a modification of the method for controlling the display in the medical system in FIG. 19.

In this embodiment, although the control signals are adjusted on the basis of the motion directions of the treating portions in the display image, alternatively, as shown in FIG. 24, the control portion 7 may calculate, on the basis of the rotational angle of the rotating operation acquired from the rotating operation information, the control parameters for associating the motion directions of the treating portions 22 and 23 on the screen 61 with the operation directions of the operating portions 41L and 41R (step SG16). By doing so, it is possible to eliminate the processing for detecting the movement of the treating portions in the display image.

The first to sixth embodiments, described above, can be employed in combination, as appropriate.

In addition, the functions of the image-processing portion 5 and the control portion 7 described in the first to sixth embodiments are realized by, for example, a computer provided with a central processing unit (CPU), a main storage device, and an auxiliary storage device. Specifically, image-processing programs and a control program are stored in the auxiliary storage device, these programs are loaded into the main storage device from the auxiliary storage device, and the above-described processing performed by the image-processing portion 5 and the control portion 7 is executed as a result of the CPU being operated in accordance with the programs.

As a result, the above-described embodiments lead to the following aspects.

One aspect of the present invention is directed to a medical system provided with: a first manipulator that is inserted into a first body cavity and that has a first treating portion and a first image-acquisition portion that captures an image of the first treating portion; a second manipulator that is inserted into a second body cavity that is different from the first body cavity and that has a second treating portion and a second image-acquisition portion that captures an image of the second treating portion; and an interface portion that is operated by an operator; a control portion that controls motions of the first treating portion and the second treating portion in accordance with operations input to the interface portion; a display portion that has a screen on which one of the first image acquired by the first image-acquisition portion and the second image acquired by the second image-acquisition portion is selectively displayed, wherein the interface portion is provided with an operating portion with which the operator inputs operation instructions for the first treating portion and the second treating portion, and an operating-target selecting portion with which the operator selectively selects one of the first treating portion and the second treating portion as an operating target of the operating portion, and the display switching portion selects, of the first image and the second image, the image acquired by the image-acquisition portion provided in the manipulator that is the same as that selected as the operating target by the operating-target selecting portion, and causes the selected image to be displayed on the screen.

With this aspect, when the operator selects, as the operating target, one of the first treating portion and the second treating portion by using the operating-target selecting portion and operates the operating portion, the selected treating portion is controlled by the control portion so as to perform motions corresponding to the operations of the operating portion. Therefore, by switching the operating target between the first treating portion and the second treating portion by using the operating-target selecting portion, it is possible for one operator to remotely operate, via the single interface portion, the first treating portion and the second treating portion disposed in the separate cavities.

In this case, the display on the screen is controlled by the display switching portion so that the image in which the operating target is captured is displayed on the screen of the display portion. Therefore, when the operator switches the operating target from the treating portion in one of the cavities to the treating portion in the other cavity, the display on the screen is also automatically switched to the image of the switched treating portion. By doing so, it is possible for one operator to smoothly operate the first treating portion and the second treating portion by causing the treating portions to cooperate with each other, while ascertaining the states of the first treating portion and the second treating portion disposed in the separate cavities on the basis of the first image and the second image, one of which is selectively displayed on the single screen.

In the above-described aspect, the first manipulator may have two of the first treating portions; the second manipulator may have two of the second treating portions; the interface portion may be provided with two of the operating portions and two of the operating-target selecting portions that correspond to the two operating portions, respectively; and, in the case in which the two operating targets selected by the two operating-target selecting portions are the first treating portion and the second treating portion, the display switching portion may select the image to be displayed on the screen in accordance with the types of the first treating portion and the second treating portion.

By doing so, it is possible to simultaneously operate the two treating portions by using the two operating portions by selecting the two treating portions as the operating targets by using the two operating-target selecting portions. In addition, in the case in which the two operating targets are a combination of the first treating portion and the second treating portion, it is possible to switch the display in accordance with the combination of the types of the two treating portions so that the image having a greater priority is displayed on the screen.

In the above-described aspect, the medical system may include a superimposing processing portion that generates a superimposed image in which the treating portion in the image that was not selected by the display switching portion is superimposed on the image selected by the display switching portion, and the display portion may display the superimposed image on the screen.

By doing so, it is possible for the operator to observe, from the superimposed image displayed on the screen, not only the treating portion serving as the operating target in one of the cavities but also the treating portion in the other cavity.

In the above-described aspect, the display portion may include a sub-screen that displays the image that was not selected by the display switching portion.

By doing so, one of the first image and the second image is displayed on the screen, and the other image is displayed on the sub-screen. Therefore, it is possible for the operator to ascertain the states of both the first treating portion in the first body cavity and the second treating portion in the second body cavity.

In the above-described aspect, the superimposing processing portion may generate a sub-superimposed image in which the treating portion in the image selected by the display switching portion is superimposed on the image that was not selected by the display switching portion, and the display portion may have a sub-screen that displays the sub-superimposed image.

By doing so, it is possible for the operator to more accurately ascertain the states of both the first treating portion and the second treating portion from the superimposed image displayed on the screen and the sub-superimposed image displayed on the sub-screen.

In the above-described aspect, the medical system may include a rotating processing portion that rotates the selected image so as to associate a motion direction of the operating target in the image selected by the display switching portion on the screen with an operation direction of the operating portion.

Alternatively, the control portion may control the motion direction of the operating target so that the motion direction of the operating target in the image selected by the display switching portion on the screen corresponds to top, bottom, left, or right direction of the operating portion.

By doing so, because the operating target in the image on the screen is moved in the direction corresponding to the direction in which the operating portion is operated by the operator, it is possible for the operator to intuitively operate the operating target.

The present invention affords an advantage in that it is possible for one operator to smoothly manipulate two treating portions by causing the two treating portions to cooperate with each other while ascertaining the states of the two treating portions disposed in separate cavities.

REFERENCE SIGNS LIST

100, 300 medical system
1 abdominal-cavity manipulator (first manipulator)
2 lumen manipulator (second manipulator)
12, 13, 22, 23 treating portion
14, 15 image-acquisition portion (first image-acquisition portion)
24, 25 image-acquisition portion (second image-acquisition portion)
4 interface portion
41L, 41R operating portion
42, 42L, 42R operating-target selecting portion
43 rotational operating portion
5 image-processing portion (superimposing processing portion, rotating processing portion)
6 display portion
61 screen, main screen
62 sub-screen
7 control portion
A abdominal cavity (first body cavity)
B lumen (second body cavity)
L abdominal-cavity image (first image)
E lumen image (second image)

The invention claimed is:

1. A medical system comprising:
a first slave manipulator inserted into a lumen of a patient, the first slave manipulator comprising a first end effector and a first camera configured to capture an image of the first end effector;
a second slave manipulator inserted into an abdominal cavity of the patient, the second slave manipulator comprising a second camera;
a first master manipulator configured to operate both the first slave manipulator and the second slave manipulator;
a second master manipulator configured to operate both the first slave manipulator and the second slave manipulator;
a first selector configured to select one of the first slave manipulator and the second slave manipulator as a first operating target of the first master manipulator;
a second selector configured to select an other of the first slave manipulator and the second slave manipulator as a second operating target of the second master manipulator;
a controller configured to control the first slave manipulator and the second slave manipulator; and
a display configured to display to the operator, wherein the controller comprises one or more processors, the one or more processors are configured to:
acquire the first operating target selected by the first selector,
acquire the second operating target selected by the second selector,
acquire a first image from one of the first camera and the second camera provided in the acquired first operating target, and
acquire a second image from an other of the first camera and the second camera provided in the acquired second operating target,
select, where the first operating target and the second operating target are different from each other, one of the first image and the second image in accordance with the types of the first slave manipulator and the second slave manipulator, and
transmit the selected first image or second image so as to be displayed on the display.

2. The medical system according to claim 1,
wherein the second slave manipulator further comprises a second end effector,
the one or more processors are configured to select, in the case in which the first operating target and the second operating target are different from each other, one of the first image and the second image in accordance with the types of the first end effector and the second end effector.

3. The medical system according to claim 2,
wherein the first slave manipulator further comprises a third end effector that is separate from the first end effector,
the second slave manipulator further comprises a fourth end effector that is separate from the second end effector, and
the first selector and the second selector are configured to selectively select one of the first to fourth end effectors.

4. The medical system according to claim 1,
wherein the first master manipulator is disposed such that the operator operates the first master manipulator with the left hand, and
the second master manipulator is disposed such that the operator operates the second master manipulator with the right hand.

5. The medical system according to claim 1,
wherein the one of more processors are configured to:
acquire a second image from the first camera or the second camera provided in the first slave manipulator or the second slave manipulator that was not selected as the acquired first operating target,
generate a third image on which the second image acquired with reference to the acquired first image is superimposed, and
transmit the third image so as to be displayed on the display.

6. The medical system according to claim 1,
wherein the display comprises a main screen and a sub-screen, and
the one or more processors are configured to:
acquire a second image from the first camera or the second camera provided in the first slave manipulator or the second slave manipulator that was not selected as the acquired first operating target,
transmit the first image so as to be displayed on the main screen, and
transmit the second image so as to be displayed on the sub-screen.

7. The medical system according to claim 5,
wherein the display comprises a main screen and a sub-screen, and
the one or more processors are configured to:
generate a fourth image by superimposing the first image acquired with reference to the acquired second image,
transmit the third image so as to be displayed on the main screen, and
transmit the fourth image so as to be displayed on the sub-screen.

8. The medical system according to claim 1,
wherein, when transmitting the acquired first image so as to be displayed on the display, the one or more processors are configured to:
transmit the first image after rotating the first image so that an operation direction of the first master manipulator and a motion direction of the first operating target in the first image achieve a predetermined correspondence relationship.

9. The medical system according to claim 1,
wherein the one or more processors are configured to:
receive an operation input from the first master manipulator,
generate a first instruction for the first operating target so that a motion direction of the first operating target in the first image and a direction of the operation input achieve a predetermined correspondence relationship, and
transmit the generated first instruction to the first operating target.

10. A control method for a medical system comprising a first slave manipulator inserted into a lumen and a second slave manipulator inserted in an abdominal cavity, the control method comprising:
acquiring one of the first slave manipulator and the second slave manipulator as a selected first operating target,
acquiring an other of the first slave manipulator and the second slave manipulator as a selected second operating target,
acquiring a first image from one of a first camera of the first slave manipulator and a second camera of the second slave manipulator provided in the selected first operating target,
acquiring a second image from an other of the first camera and the second camera provided in the acquired second operating target,
selecting one of the first image and the second image in accordance with the types of the first slave manipulator and the second slave manipulator, where the first operating target and the second operating target are different form each other, and
transmitting the selected first image or second image so as to be displayed on the display.

11. The control method for a medical system according to claim 10,
wherein the first slave manipulator further comprises a first end effector,
the second slave manipulator further comprises a second end effector, and the control method comprising:
selecting one of the first image and the second image in accordance with the types of the first end effector and the second end effector, in the case in which the first operating target and the second operating target are different from each other.

12. The control method for a medical system according to claim 11,
wherein the first slave manipulator further comprises a third end effector,
the second slave manipulator further comprises a fourth end effector, and
one of the first to fourth end effectors are selectively selected as the first operating target and the second operating target, respectively.

13. The control method for a medical system according to claim 10, further comprising:
acquiring a second image from the first camera or the second camera provided in the first slave manipulator or the second slave manipulator which was not selected as the acquired first operating target,
generating a third image by superimposing the second image acquired with reference to the acquired first image, and
transmitting the third image so as to be displayed on the display.

14. The control method for a medical system according to claim 10,
wherein the display comprises a main screen and a sub-screen, the control method comprising:
acquiring a second image from the first camera or the second camera provided in the first slave manipulator or the second slave manipulator which was not selected as the acquired first operating target,
transmitting the first image so as to be displayed on the main screen, and
transmitting the second image so as to be displayed on the sub-screen.

15. The control method for a medical system according to claim 13,
wherein the display comprises a main screen and a sub-screen, the control method comprising:
generating a fourth image by superimposing the first image acquired with reference to the acquired second image,
transmitting the third image so as to be displayed on the main screen, and
transmitting the fourth image so as to be displayed on the sub-screen.

16. The medical system according to claim 1, wherein when the first image is selected, the one or more processors are further configured to:
rotate the first image so that an operation direction of the first master manipulator for operating the first operating target and a motion direction of the first operating target in the first image achieve a predetermined correspondence relationship, and
transmit the rotated first image so as to be displayed on the display.

* * * * *